(12) United States Patent
Zavadtsev et al.

(10) Patent No.: US 7,491,958 B2
(45) Date of Patent: Feb. 17, 2009

(54) RADIOGRAPHIC INSPECTION SYSTEM FOR INSPECTING THE CONTENTS OF A CONTAINER HAVING DUAL INJECTOR AND DUAL ACCELERATING SECTION

(75) Inventors: Alexandre A. Zavadtsev, Reutov (RU); Gary F. Bowser, Auburn, IN (US)

(73) Assignee: ScanTech Holdings, LLC, Atlanta, GA (US)

( * ) Notice: Subject to any disclaimer, the term of this patent is extended or adjusted under 35 U.S.C. 154(b) by 0 days.

(21) Appl. No.: 10/569,752

(22) PCT Filed: Aug. 27, 2004

(86) PCT No.: PCT/US2004/028030

§ 371 (c)(1),
(2), (4) Date: Feb. 26, 2007

(87) PCT Pub. No.: WO2005/022554

PCT Pub. Date: Mar. 10, 2005

(65) Prior Publication Data

US 2007/0274445 A1    Nov. 29, 2007

Related U.S. Application Data

(60) Provisional application No. 60/498,428, filed on Aug. 27, 2003.

(51) Int. Cl.
*G01N 21/86* (2006.01)
(52) U.S. Cl. .................. 250/559.4; 250/221
(58) Field of Classification Search ............. 250/559.4, 250/559.34, 221, 492.21, 492.23; 315/500, 315/505, 507; 378/138, 83, 88; 356/427, 356/428, 239.5, 239.6, 240.1
See application file for complete search history.

(56) References Cited

U.S. PATENT DOCUMENTS 4,118,653 A * 10/1978 Vaguine .................. 315/5.41
6,920,197 B2    7/2005 Kang et al.

* cited by examiner

*Primary Examiner*—Que T Le
(74) *Attorney, Agent, or Firm*—R. Stevan Coursey; Coursey IP Law, PC

(57) ABSTRACT

A radiographic inspection system for inspecting subject objects using charged particle beams having pulses of charged particles with different energy levels from pulse to pulse. A phase shifter thereof enables adjustment of the RF power delivered to first and second accelerating sections thereof from a single RF source without adjustment of the RF power generated by the RF source. The system also enables the generation of images of the contents of a container from multiple directions and in multiple planes, and allows the discrimination of materials present in the container.

12 Claims, 6 Drawing Sheets

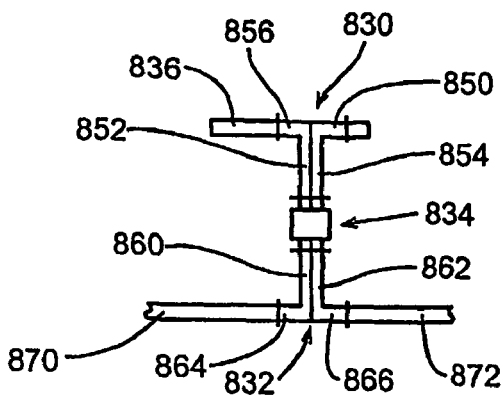
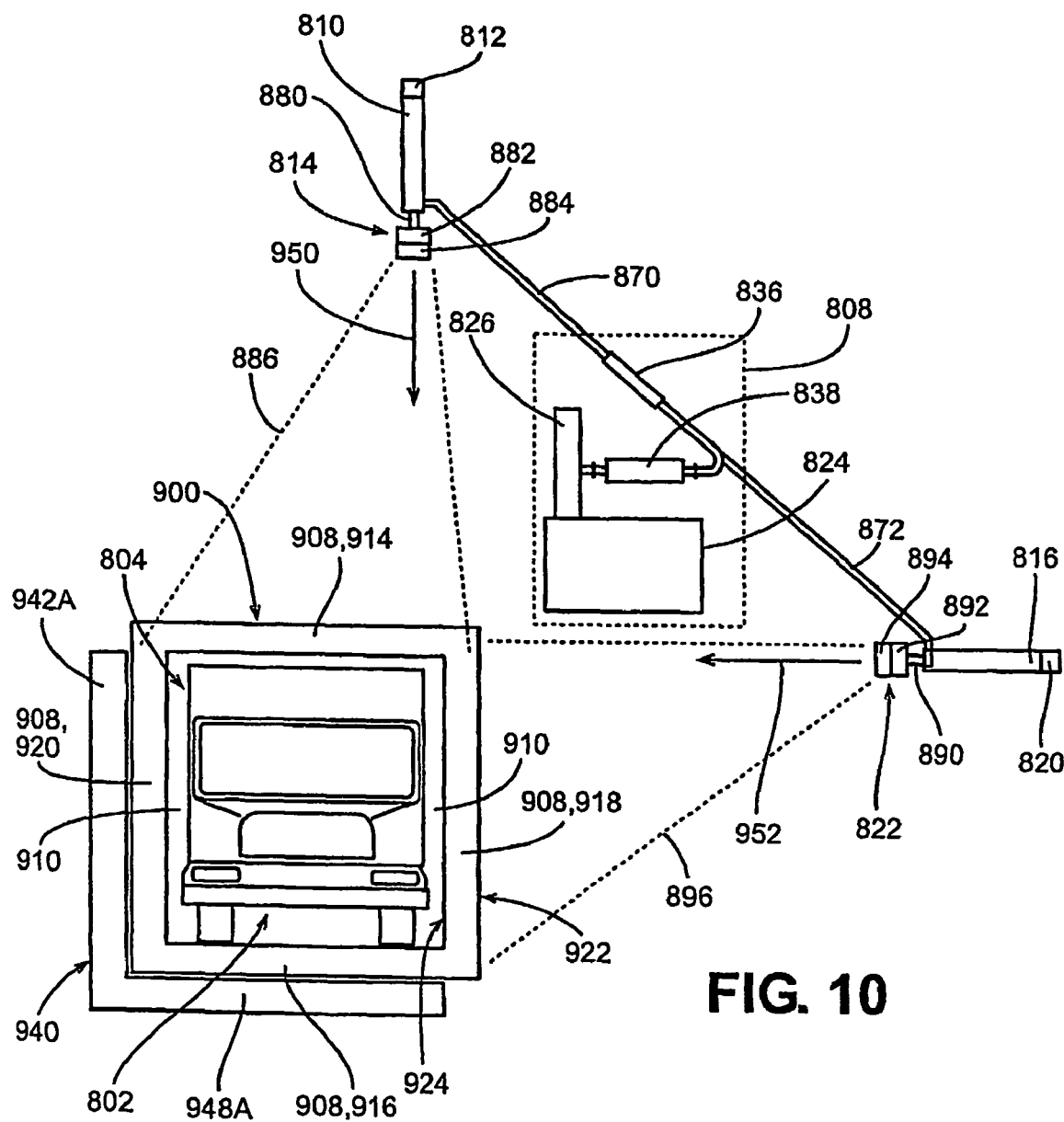
FIG. 9
FIG. 10

RADIOGRAPHIC INSPECTION SYSTEM FOR INSPECTING THE CONTENTS OF A CONTAINER HAVING DUAL INJECTOR AND DUAL ACCELERATING SECTION

CROSS REFERENCE TO RELATED APPLICATION

This application claims the benefit of priority to U.S. provisional application Ser. No. 60/498,428 which is entitled "RADIOGRAPHIC INSPECTION SYSTEM" and was filed on Aug. 27, 2003.

FIELD OF THE INVENTION

The invention relates, generally, to the field of charged particle accelerator systems and methods, and, more specifically, to charged particle accelerator systems and methods capable of producing successive pulses of charged particles having different energy levels for use in multi-direction, multi-plane inspection systems.

BACKGROUND OF THE INVENTION

In recent years, the proliferation of international terrorism has spurred concerns over the contents of cargo containers which are received from foreign countries by land or sea as such cargo containers may include explosives, weapons of mass destruction, or other items that may be harmful to individuals and/or property. Existing inspection systems utilize high energy X-rays to produce visual images of the contents of cargo containers. The high energy X-rays are, typically, obtained by generating a beam of highly energized electrons with a standing wave linear accelerator and directing the beam at a conversion target that transforms the electrons into high energy X-rays. The cargo containers are then exposed to the high energy X-rays and data is collected by detectors positioned behind the cargo containers after the high energy X-rays pass through the items in the cargo containers. However, the collected data is inadequate to identify or discriminate between different materials present in the cargo containers and, hence, such inspection systems provide only visual images of the contents of cargo containers.

To identify and discriminate between different materials in the cargo containers, it is necessary to expose the cargo containers to high energy X-rays having different energy spectra and to appropriately evaluate data collected during such exposure. The generation of such high energy X-rays may be accomplished in a manner similar to that employed for the generation of high energy X-rays having a single energy spectra. That is, a beam of highly energized electrons may be obtained by generating a beam of highly energized electrons having different energy spectra and directing the beam at a conversion target to produce the high energy X-rays having different energy spectra. Unfortunately, the generation of such a beam of highly energized electrons having different energy spectra has proven to be problematic.

A number of approaches have been attempted in the past to vary the energy of a beam of electrons emerging from a particle accelerator to produce a beam of electrons having different energy spectra. In a first approach, the radio frequency (RF) power supplied to the accelerating cavities of a standing wave linear accelerator from the accelerator's RF power source is varied through use of an attenuator located in the waveguide connecting the RF power source to the accelerating cavities, thereby varying the amplitude of the accelerating field in the cavities and varying the energy level of the accelerator's output beam of electrons. However, varying the RF power in this manner causes the beam produced by the accelerator to have a large energy spread, and consequently, the efficiency of the particle accelerator is decreased.

In a second approach, the energy of the beam of electrons produced by a standing wave linear accelerator is regulated by varying the RF power supplied to the accelerator without the use of an attenuator. Such accelerator has two accelerating sections and a 3 dB waveguide hybrid junction which delivers equal RF power to each accelerating section. The accelerator, however, suffers from the same disadvantages as suffered by the accelerator of the first approach described above. The decrease in the RF power supplied to the accelerating sections directly causes the resulting electron beam to have a lower energy. The decrease in the RF power supplied to the first accelerating section weakens the accelerating field in the first accelerating section, thereby reducing the number of electrons that are captured and tightly bunched. Due at least in part to the weakened accelerating electric field, there is a decrease in the overall efficiency of the accelerator.

According to a third approach, RF power is supplied to the traveling wave accelerating section of a particle accelerator having a traveling wave accelerating section coupled to a standing wave accelerating section with an attenuator and variable phase shifter interposed therebetween. The RF power travels through the traveling wave accelerating section and creates an accelerating field therein. Before entering the standing wave accelerating section, the residual RF power from the traveling wave accelerating section is attenuated by the attenuator, thereby reducing the amplitude of the accelerating field in the standing wave accelerating section. The variable phase shifter may also vary the phase of the residual RF power and, hence, the phase of the accelerating field in the standing wave accelerating section. By controlling both amplitude and phase of the accelerating field in the standing wave accelerating section, the electron energy of the beam exiting the particle accelerator is controlled. Unfortunately, this approach is also inadequate because of the resulting ungrounded electromagnetic energy loss in the attenuator at amplitude control and in the standing wave accelerating section at phase control.

Two other approaches involve the mechanical adjustment of the magnetic field in a coupling cavity. In the first mechanical adjustment approach, a rod is inserted into one external coupling cavity of a side-coupled biperiodic accelerating structure with external coupling cavities. Insertion of the rod into the external coupling cavity changes the mode of oscillation therein. When the mode of oscillation in the coupling cavity is changed, an additional phase shift of one hundred eighty degrees results in a phase difference between the accelerating fields, of two of the adjacent accelerating cavities. As a consequence, charged particles are accelerated near the beginning of the accelerating structure and decelerated near the end of the accelerating structure.

In the second mechanical adjustment approach, one of the coupling cavities of a side-coupled biperiodic accelerating structure is constructed such that it may be made asymmetrical by a mechanical adjustment. In this approach, two rods are inserted at opposite sides of the coupling cavity. By asymmetrically inserting the rods, the oscillation mode and the frequency remain unchanged in the coupling cavity, but the magnetic field distribution increases on the side in which the rod is inserted more, and thus, the coupling coefficient to the adjacent accelerating cavity is greater at such side. Although adjustment of the rods enables the output particle energy to be varied, the mechanical process by which the rods are adjusted is extremely slow and is inadequate for applications that require an output beam of electrons that must be rapidly varied between energy levels. Moreover, there is an inherent risk of sparking during sliding of the rods within the cavity.

Therefore, there exists in the industry, a need for particle accelerator systems and methods which are operable to produce particle beams with different energy levels over a wide range of energy levels such that the beam energy level may be changed rapidly between one energy level and another, that makes maximal use of electromagnetic power to accelerate charged particles, that enables the multi-direction, multi-plane imaging of the contents of a vehicle, container, or volume, that enables the discrimination of different materials present in a vehicle, container, or volume, and that addresses these and other problems or difficulties which exist now or in the future.

SUMMARY OF THE INVENTION

Broadly described, the present invention comprises particle accelerator systems, including apparatuses and methods, for producing charged particle beams having pulses of charged particles that have different energy levels from pulse to pulse for use in inspection systems. More particularly, the present invention comprises particle accelerator systems, including apparatuses and methods, for producing charged particle beams having pulses of charged particles that have different energy levels from pulse to pulse by independently adjusting the amount of RF power delivered to first and second accelerating sections thereof without adjusting the amount of RF power generated by an RF source thereof.

According to a first embodiment, a particle accelerator system includes an RF drive subsystem having an RF source coupled to an amplifier and a phase shifter so as to enable adjustment of the accelerating field created in an accelerating section without adjusting the power output from the RF source. The ratio of the amplitudes of the RF waves provided to the accelerating sections is regulated by shifting the phase of the RF waves delivered to the second accelerating section relative to the phase of the RF waves of the first accelerating section with a phase shifter. Because the magnitude, or strength, of the accelerating fields in the accelerating sections depends on the RF power provided, respectively, to each of the accelerating sections and because the RF power provided to each of the accelerating sections is based on the amplitudes of the RF waves provided thereto, shifting the phase of the RF waves for the second accelerating section enables changing of the RF power provided to the second accelerating section and of the magnitude of the accelerating field of the second accelerating section relative to the magnitude of the accelerating field of the first accelerating section.

In a first mode of operation of the first embodiment, the particle accelerator system includes a conventional phase shifter that is tuned prior to operation of the particle accelerating system to always perform a fixed phase shift on received RF waves. However, in a second mode of operation, the phase shifter comprises a high-speed phase shifter of a plurality of high-speed phase shifters that are capable of shifting the phase of received RF waves between at least two phases and between successive pulses of charged particles. According to a second embodiment, a high-speed phase shifter interposed and connected to two 3 dB waveguide hybrid junctions functions as a variable phase shifter so as to regulate the ratio of RF power supplied to first and second accelerating sections without varying the power output from the RF source. In a high energy mode of operation (i.e., in which charged particles having a high energy level are produced), the phase of the RF waves provided to the second accelerating section is selected such that the accelerating fields in the accelerating sections are substantially equal. However, in a low energy mode of operation (i.e., in which charged particles having a low energy level are produced), the phase of the RF waves provided to the second accelerating section is changed to increase the portion of RF source power that is distributed to the first accelerating section. Simultaneously, to compensate for the increased power delivered to the first accelerating section, the injection current is increased so that strength of the accelerating field in the first accelerating section equals the strength of the accelerating field in the first accelerating section in the high energy mode. As a consequence, the incremental change in the energy level of the charged particles in the first accelerating section in both low and high energy modes is substantially the same.

The RF power supplied to the second accelerating section in low energy mode is significantly lower than the RF power supplied to the second accelerating section in the high energy mode. Because the RF power supplied to the second accelerating section is decreased in the low energy mode and because the injection current is increased in the low energy mode, the energy provided to the second accelerating section is lower and, hence, the strength of the accelerating field in the second accelerating section is lower than in high energy mode. As a consequence, the incremental energy increase in the energy level of the charged particles in the second accelerating section in low energy mode is substantially lower than the incremental energy increase in the energy level of the charged particles in the second accelerating section in high energy mode.

According to a third embodiment, a particle accelerator system includes an RF drive subsystem having an RF source coupled to two 3 dB waveguide hybrid junctions with a phase shifter interposed between the 3 dB waveguide hybrid junctions so as to provide RF power to multiple accelerating sections from a single RF source and to enable adjustment of the RF power supplied to the accelerating sections without adjusting the power output from the RF source. The ratio of the amplitudes of the RF waves provided to the accelerating sections is regulated by shifting the phase of the RF waves delivered to a first accelerating section with a phase shifter relative to the phase of the RF waves delivered to another accelerating section. Because the magnitude, or strength, of the accelerating fields in the accelerating sections depends on the RF power provided, respectively, to each of the accelerating sections and because the RF power provided to each of the accelerating sections is based on the amplitudes of the RF waves provided thereto, shifting the phase of the RF waves for a second accelerating section enables changing of the RF power provided to the second accelerating section and of the magnitude of the accelerating field of the second accelerating section relative to the magnitude of the accelerating field of a first accelerating section. By changing the amount of RF power supplied to the accelerating sections on an alternating pulse by pulse basis through use of the phase shifter, the energy levels of pulses of charged particles emitted from each accelerating section alternate between energy levels. By further positioning the accelerating sections such that bremsstrahlung produced from such pulses of charged particles impinge on a subject object from multiple directions or in multiple planes, a radiographic system incorporating such a particle accelerator system is operable to generate images of the contents of the subject object and to discriminate materials present within the subject object.

BRIEF DESCRIPTION OF THE DRAWINGS

FIG. 9 displays a side, elevational pictorial view of a portion of an RF drive subsystem of the radiographic inspection system of FIG. 8.

FIG. 10 displays a front, elevational pictorial view of the radiographic inspection system of FIG. 8.

DETAILED DESCRIPTION OF THE INVENTION

Figure 1:
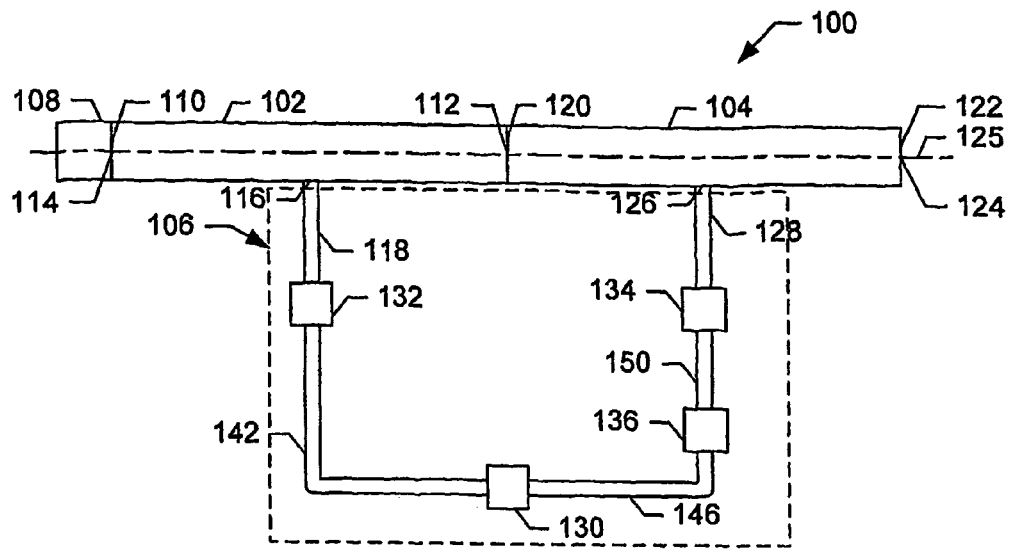
FIG. 1 displays a schematic block diagram representation of a particle accelerator system in accordance with a first embodiment of the present invention.

Referring now to the drawings in which like numerals represent like elements or steps throughout the several views, FIG. 1 displays a schematic block diagram representation of a particle accelerator system 100 in accordance with a first embodiment of the present invention. The particle accelerator system 100 comprises a first accelerating section 102, a second accelerating section 104, an RF drive subsystem 106, and an injector 108. Preferably, the first and second accelerating sections 102, 104 comprise standing-wave accelerating sections 102, 104 having a biperiodic accelerating structure which are operable to accelerate charged particles through the transfer of energy from RF power provided to the accelerating sections 102, 104 by the RF drive subsystem 106.

The first accelerating section 102 has a first end 110 and a second end 112. The injector 108 is positioned proximate the first end 110 of the first accelerating section 102 and is connected to an input port 114 of the first accelerating section 102. The injector 108 is operable to generate charged particles and to emit them in a pulsed mode of operation as pulses of charged particles, into the first accelerating section 102 through input port 114. Preferably, the charged particles comprise electrons. The first accelerating section 102 defines an oblong-shaped slot 116 which couples the first accelerating section 102 to a feeder waveguide 118 of the RE drive subsystem 106 to enable RF power to propagate from the feeder waveguide 118 into and through the first accelerating section 102.

Similar to the first accelerating section 102, the second accelerating section 104 has a first end 120 and a second end 122. The second accelerating section 104 is connected to the first accelerating section 102 to enable charged particles to travel between the first and second accelerating sections 102, 104. The second accelerating section 104 includes an output port 124 located at the second end 122 of the second accelerating section 104. A longitudinal axis 125 of the particle accelerator system 100 extends between, and is defined by, the input port 114 and the output port 124 thereof. The output port 124 is adapted to direct a beam of charged particles from the second accelerating section 104 (and, hence, from the particle accelerator system 100) toward a desired target or other object. The second accelerating section 104 defines an oblong-shaped slot 126 which couples the second accelerating section 104 to a feeder waveguide 128 of the RE drive subsystem 106 to allow RF power to propagate from the feeder waveguide 128 into and through the second accelerating section 104.

The RF drive subsystem 106 comprises a radio frequency (RF) source 130, a first amplifier 132, a second amplifier 136, and a phase shifter 134. The RF source 130 is operable to generate RF power in the form of pulses of RF waves, having an appropriate frequency, power level, and pulse repetition rate, in a pulsed mode of operation synchronized with the emission of charged particles by injector 108 and to output such RF power via output coaxial lines 142, 146. Preferably, the RF source 130 comprises an RF generator such as a solid state microwave generator which generates 400 W of RF power in the form of pulses of RF waves having a frequency of 2.8 0 Hz and a pulse repetition rate of 500 Hz.

The first amplifier 132 is connected to the RF source 130 by coaxial line 142 and is adapted to receive RF power generated and output by RF source 130 via coaxial line 142. The first amplifier 132 is operable to amplify the received RF power, to preferably, 2.5 MW and to deliver the amplified RF power to the first accelerating section 102 through feeder waveguide 118 and oblong-shaped slot 116 so as to create an accelerating field (i.e., the strength or magnitude of which is determined by the amplified RF power) in the first accelerating section 102 of particle accelerator system 100. Preferably, amplifier 132 comprises a klystron. It should be understood that the scope of the present invention includes other forms of amplifiers or other appropriate devices for amplifying RF power.

The second amplifier 136 is connected to the RF source 130 by coaxial line 146 and is adapted to receive RF power generated and output by RF source 130 via coaxial line 146. The second amplifier 136 is operable to amplify the received RF power, to preferably MW, and to deliver the amplified RF power to the phase shifter 134 via waveguide 150. 10 Preferably, the second amplifier 136 includes a klystron. It should be understood that the scope of the invention includes other forms of amplifiers or other appropriate devices for amplifying RF power.

The phase shifter 134 is connected to the second accelerating section 104 by waveguide 128. Phase shifter 134 is operable to receive RF power amplified by the second amplifier 136, to change the phase of the RF waves thereof, and to supply the phase shifted RF power to the second accelerating section 104 via connected waveguide 128. In a first mode of operation described below, the phase shifter 134 comprises a conventional phase shifter that is tuned prior to operation of the particle accelerating system 100 to always shift the phase of the received RF waves of the pulses of RF waves to a single fixed phase. However, in a second mode of operation described below, the phase shifter 134 comprises a high-speed phase shifter such as, for example, one of the phase shifters 200, 300, 500, 600 illustrated in FIGS. 2, 3, 5, and 6 described below, which are capable of shifting the phase of the RF waves of the pulses of received RF waves to one of at least two phases and to do so in synchronization with pulses of charged particles emitted by injector 108.

It should be noted that the strength, or magnitude, of the accelerating field in the first and second accelerating sections 102, 104 depends on the RF power provided thereto. It should also be noted that the provided RF power depends on the amplitudes of the RF waves of the pulses of RF waves. Therefore, changing the gain of the second amplifier 136 and, hence, the RF power supplied to the second accelerating section 104 relative to the first accelerating section 102, changes the strength of the accelerating field in the second accelerating section 104, relative to the first accelerating section 102. As a consequence, the incremental energy added to the charged particles in the second accelerating section 104 relative to the first accelerating section 102 is also changed.

In a first method of operation, the injector 108 of the particle accelerating system 100 generates and emits charged particles (preferably, electrons) into the first accelerating section 102. Concurrently, the RF source 130 of the RF drive subsystem 106 generates RF power in a pulsed mode of operation synchronized with the emission of charged particles by injector 108 and outputs such RF power, including pulses of RF waves, to the first amplifier 132 via coaxial line 142. The first amplifier 132 receives the generated RF power output by RF source 130 and amplifies the received RF power to a desired power level (preferably, 2.5 MW). The first amplifier 132 then delivers the amplified RE power to the first accelerating section 102 via feeder waveguide 118 and through oblong-shaped slot 116. The amplified RF power creates an accelerating field in the first accelerating section 102 of particle accelerator system 100.

As the RF source 130 generates and delivers RF power to the first amplifier 132, the RF source 130 concurrently generates and delivers RF power to the second amplifier 136 via coaxial line 146. The second amplifier 136 amplifies the received RF power and delivers the amplified RF power to the phase shifter 134 via waveguide 150. In this first method of operation, the phase shifter 134 comprises a conventional phase shifter that performs a predetermined and fixed phase shift to the RF waves of the received pulses of RF waves. The phase shifted RF power exits phase shifter 134, via waveguide 128, and is received by the second accelerating section 104 through oblong-shaped slot 126. The phase shifter 134 delivers the amplified and phase shifted RF power through waveguide 128 and oblong-shaped slot 126 to the second accelerating section 104, and the received RF power creates an accelerating field in the second accelerating section 104.

Alternatively, the phase shifter 134 may be connected between RF source 130 and the second amplifier 136. In such case, the phase shifter 134 is connected via a coaxial line rather than a rectangular waveguide.

In the first method of operation, the particle accelerating system 100 alternately operates in a high energy mode and a low energy mode to produce and output charged particle pulses having energy levels which alternate between high energy and low energy levels. When operating in the high energy mode, the phase of the RF power as adjusted by phase shifter 134 is selected so that the strength of the accelerating field created in the second accelerating section 104 is maximized with the result being that the charged particles receive a maximum incremental increase in energy as they are accelerated by the second accelerating section 104.

When operating in the low energy mode, the first amplifier 132 is adjusted such that the generated RF power delivered to the first accelerating section 102 by first amplifier 132 is amplified more than the generated RF power delivered to the first accelerating section 102 by the first amplifier 132 when operating in the high energy mode. Concurrently, the rate at which the injector 108 emits particles into the first accelerating section 102, or in other words, the particle injection current, is increased in order to maintain the strength of the accelerating field of the first accelerating section 102 at the same strength as when operating in the high energy mode. Additionally, the second amplifier 136 is adjusted such that the RF power delivered by the RF source 130 to the phase shifter 134 and then to the second accelerating section 104 is less than the phase shifted RF power delivered by the second amplifier 136 to the second accelerating section 104 during operation in the high energy mode.

Through use of the first method of operation, the strength of the accelerating field created in the first accelerating section 102 is substantially identical in both the high and low energy modes. Thus, the quality and efficiency of particle bunching and capturing that occurs in the first accelerating section 102 remains substantially the same in both high and low energy modes. However, in the second accelerating section 104, the incremental change in the amount of energy each charged particle receives in the low energy mode is significantly lower than the incremental change in the amount of energy each charged particle receives in the high energy mode. This result occurs because in the low energy mode, the RF power delivered to the second accelerating section 104 is reduced as compared to the RF power delivered to the second accelerating section 104 in the high energy mode in order to compensate for the increased particle injection current. Because the charged particle energy decrease in the low energy mode accompanies a beam current increase, the beam power levels in the high and low energy modes are substantially equal to one another, which has typically been required for precise bremsstrahlung registration by detectors in cargo container inspection systems. Thus, through use of the first method of operation, the particle accelerating system 100 enables rapid alternation between high and low energy modes for successive pulses of synchronized RF waves and injected particles.

In the second method of operation of the first embodiment, the particle accelerating system 100 alternately operates in a high energy mode and a low energy mode to produce and output pulses of charged particles which alternately have a high energy level and a low energy level. In both the high and low energy modes, the RF power amplification provided by amplifiers 132, 136 remains constant. That is, the amount by which the amplifiers 132, 136 amplify the received RF power remains identical in both the high and the low energy modes. Moreover, the particle injection current also remains constant in both the high and the low energy mode. However, phase shifter 134 shifts the phase of the generated RF power (i.e., the phase of the RF waves present in the RF wave pulses) provided thereto alternately between two phases and does so in synchronization with and for alternating pulses of charged particles emitted by injector 108. To do so quickly and in synchronization with pulses, the phase shifter 134 comprises one of the high-speed phase shifters 200, 300, 500, 600 illustrated in FIGS. 2, 3, 5, and 6 described below and operates in accordance with the corresponding method of operation thereof. In this second method of operation, the difference in the resulting beam power level is greater between pulses than it is using the first method of operation. However, even though there is a greater differential between the energy levels of alternating pulses of charged particles in the output beam, the differential may be acceptable if the particle accelerator system 100 is used in a cargo container inspection system with a detector having a sufficient dynamic range for bremsstrahlung detection.

Figure 2:
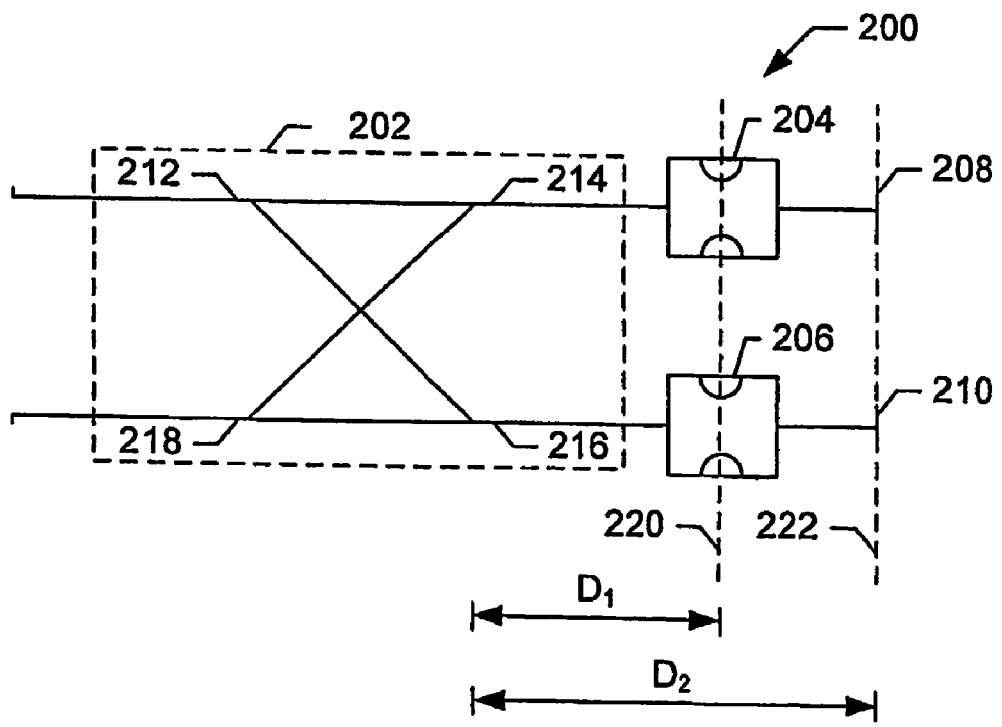
FIG. 2 displays a schematic block diagram representation of a first form of a high speed phase shifter, which is employable as a phase shifter in accordance with the first and second embodiments of the present invention.

FIG. 2 displays a schematic block diagram representation of a first form of a high-speed phase shifter 200, which is employable as a phase shifter 134 in accordance with the first embodiment of the present invention. High-speed phase shifter 200 comprises a 3 dB waveguide hybrid junction 202, two waveguide dischargers 204, 206, and two waveguide shorting devices 208, 210. The 3 dB waveguide hybrid junction 202 includes an input waveguide 212 that is connectable to an external waveguide for the receipt of pulses of input RF waves therefrom. The 3 dB waveguide hybrid junction 202 also includes first, second and third output waveguides 214, 216, 218 with the third output waveguide 218 being connectable to an external waveguide for the output of pulses of phase shifted RF waves produced by the high-speed phase shifter 200. The first and second output waveguides 214, 216 are connected to respective waveguide dischargers 204, 206. Waveguide shorting devices 208, 210 are connected, respectively, at the ends of the waveguide dischargers 204, 206 and are substantially perpendicular to the longitudinal axes of the first and second output waveguides 214, 216 of the 3 dB waveguide hybrid junction 202. The waveguide shorting devices 208, 210 create, or define, a shorting plane 222 extending therethrough which, as illustrated in FIG. 2, is located at a distance, $D_2$, from the first and second output waveguides 214, 216 of the 3 dB waveguide hybrid junction 202 and is substantially perpendicular to the longitudinal axes thereof.

The waveguide dischargers 204, 206 are operable and switchable between a first state and a second state. In the first state, the waveguide dischargers 204, 206 emit an electrical discharge that creates, or defines, an effective shorting plane 220 which, as illustrated in FIG. 2, is located at a distance, $D_1$, from the first and second output waveguides 214, 216 of the 3 dB waveguide hybrid junction 202 and is substantially perpendicular to the longitudinal axis thereof. In the second state, the waveguide dischargers 204, 206 do not emit an electrical discharge 204, 206 and, hence, no effective shorting plane 220 is created or defined by the waveguide dischargers 204, 206.

In operation, the phase angle, $\phi$, of the phase shifted RF waves of a pulse of phase shifted RF waves output by the high-speed phase shifter 200 depends on the distance, D, between the first and second output waveguides 214, 216 of the 3 dB waveguide hybrid junction 202 and the particular shorting plane 220, 222 used by phase shifter 200. Therefore, by alternately switching the waveguide dischargers 204, 206 on and off between the first and second states thereof at a rate substantially equal to the rate at which pulses of RF waves are received by the input waveguide 212, one of shorting plane 220 or effective shorting plane 222 is selected for use to change the phase angle, $\phi$, of the received RF waves. Thus, when the waveguide dischargers 204, 206 are switched-on and are in their first state, effective shorting plane 220 is used by phase shifter 200 to change the phase of the received RF waves with the phase angle, $\phi$, of the output phase shifted RF waves being determined by distance $D_1$. When the waveguide dischargers 204, 206 are switched-off and are in their second state, shorting plane 222 is selected for use to change the phase of the received RF waves with the phase angle, $\phi$, of the output phase shifted RF waves being determined by distance $D_2$. By alternately switching the waveguide dischargers 204, 206 between their first and second states, the phase angle, $\phi$, of the output phase shifted RF waves in each output pulse of output phase shifted RF waves alternately switches between a first phase angle, $\phi_1$, and a second phase angle, $\phi_2$, Because the waveguide dischargers 204, 206 are switchable alternately between the first and second states thereof at a rate substantially equal to and synchronized with the rate at which pulses of charged particles are emitted by injector 108 and pulses of RF waves are received by input waveguide 212, the high-speed phase shifter 200 is operable to produce pulses of output phase shifted RF waves having a desired phase angle, $\phi$, at a rate required by the particle accelerator system 100 for changing of the accelerating field of the second accelerating section 104 thereof according to whether a high energy pulse of charged particles or a low energy pulse of charged particles is presently being generated by the particle accelerator system 100 (i.e., according to whether the particle accelerator system 100 is operating in a high energy mode or in a low energy mode).

Figure 3C:
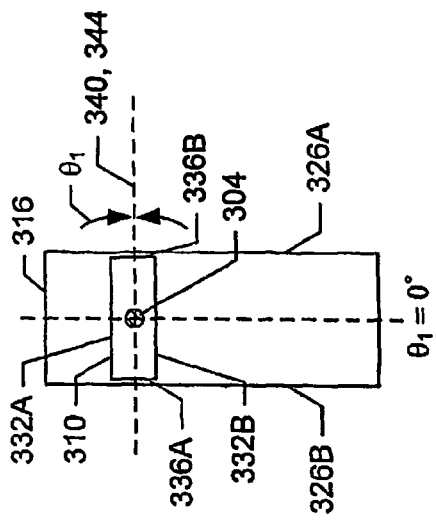
FIG. 3C displays a schematic partial cross-sectional view of the second form of a high-speed phase shifter taken along lines 3C-3C of FIG. 3A.
Figure 3E:
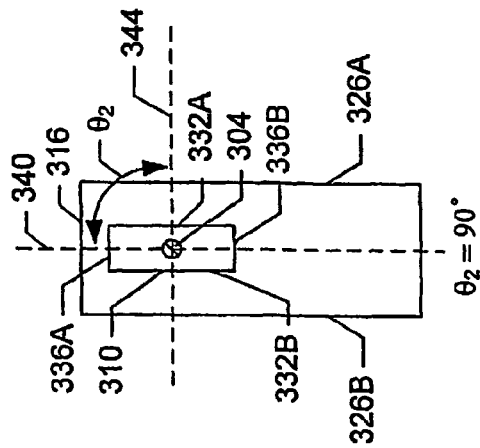
FIG. 3E displays a schematic partial cross-sectional view of the second form of a high-speed phase shifter taken along lines 3E-3E of FIG. 3A.
Figure 3B:
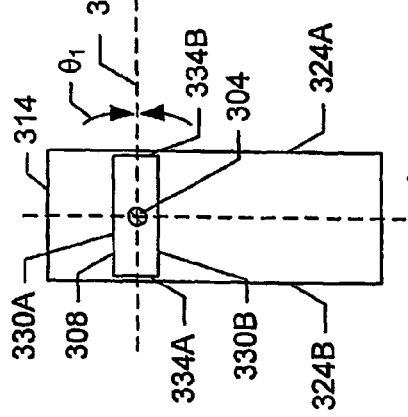
FIG. 3B displays a schematic partial cross-sectional view of the second form of a high-speed phase shifter taken along lines 3B-3B of FIG. 3A.
Figure 3D:
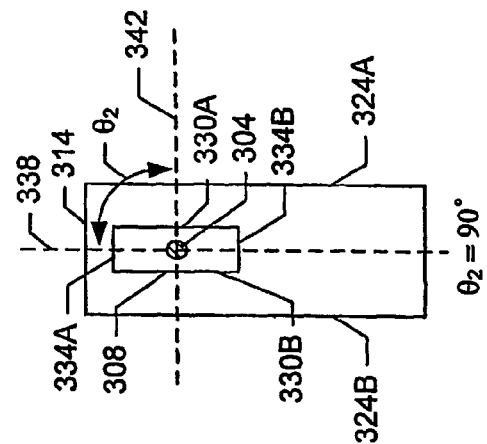
FIG. 3D displays a schematic partial cross-sectional view of the second form of a high-speed phase shifter taken along lines 3D-3D of FIG. 3A.
Figure 3A:
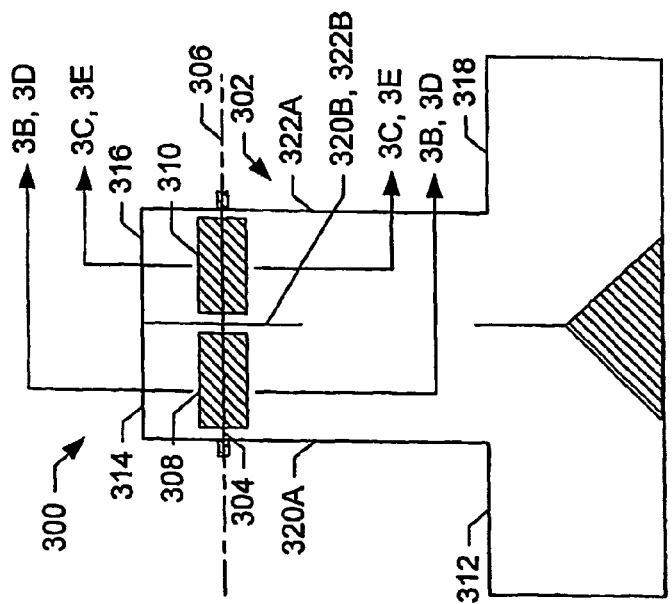
FIG. 3A displays a schematic cross-sectional view of a second form of a high-speed phase shifter, which is employable as a phase shifter in accordance with the first and second embodiments of the present invention.

FIG. 3A displays a schematic cross-sectional view of a second form of a high-speed phase shifter 300, which is employable as a phase shifter 134 in accordance with the first embodiment of the present invention. High-speed phase shifter 300 comprises a 3 dB waveguide hybrid junction 302, a rotatable shaft 304 which defines a longitudinal axis 306, and two asymmetric rotary reflectors 308, 310 (which are, essentially, shorting devices) secured to the rotatable shaft 302 for rotation with the rotatable shaft 302 about the longitudinal axis 306 at a an appropriate rate. Preferably, the rotary reflectors 308, 310 are constructed of a dielectric material. The 3 dB waveguide hybrid junction 302 includes an input waveguide 312 that is connectable to an external waveguide for the receipt of pulses of input RF waves therefrom. The 3 dB waveguide hybrid junction 302 also includes first, second and third output waveguides 314, 316, 318 with the third output waveguide 318 being connectable to an external waveguide for the output of pulses of phase shifted RF waves produced by the high-speed phase shifter 300.

The first and second output waveguides 314, 316 of the 3 dB waveguide hybrid junction 302 have, preferably, a rectangular cross-sectional shape and have respective narrow sides 320A, 320B, 322A, 322B and respective wide sides 324A, 324B, 326A, 326B (see FIGS. 3A, 3B, 3C). Preferably, the first and second output waveguides 314, 316 share a common wall therebetween that forms their respective narrow sides 320B, 322B. Reference planes 342, 344 are defined, preferably, as being perpendicular (see FIGS. 3B and 3C) to respective wide sides 324A, 324B, 326A, 326B and extending through longitudinal axis 306. Rotatable shaft 304, preferably, extends between and through narrow sides 320A, 320B, 322A, 322B of the first and second output waveguides 314, 316 of 3 dB waveguide hybrid junction 302. The rotary reflectors 308, 310 are, preferably, secured to the rotatable shaft 304 such that rotary reflector 308 is positioned for rotation within the first output waveguide 314 and rotary reflector 310 is positioned for rotation within the second output waveguide 316. The rotary reflectors 308, 310, preferably, comprise rectangular-shaped plates having rectangular-shaped cross-sections with a longitudinally-extending hole 328 defined therethrough for receipt of rotatable shaft 304 and are, preferably, manufactured from copper or another appropriate material. The dimensions of the rotary reflectors 308, 310 are selected to enable the rotary reflectors 308, 310 to be freely rotated, respectively, within the first and second output waveguides 314, 316 about longitudinal axis 306 upon rotation of rotatable shaft 304. It should be understood that the scope of the present invention comprises rotary reflectors 308, 310 of different forms having different shaped cross-sections and rotary reflectors 308, 310 that are manufactured wholly, or in part, from different materials.

As illustrated in the schematic partial cross-sectional views of FIGS. 3B and 3C respectively taken along lines 3B-3B and 3C-3C of FIG. 3A, the rotary reflectors 308, 310 have respective long sides 330A, 330B, 332A, 332B and respective short sides 334A, 334B, 336A, 336B. The rotary reflectors 308, 310 are, preferably, positioned about rotatable shaft 304 at the same angular orientation relative thereto such that rotary reflector 310 is hidden behind rotary reflector 308 in FIGS. 3B and 3C and such that the long sides 330A, 330B of rotary reflector 308 are coplanar with the long sides 332A, 332B of rotary reflector 310 and the short sides 334A, 334B of rotary reflector 308 are coplanar with the short sides 336A, 336B of rotary reflector 310. Respective reference planes 338, 340 are defined as extending through longitudinal axis 306 and being parallel, respectively, to long sides 330A, 330B, 332A, 332B of the rotary reflectors 308, 310. It should be understood that the scope of the present invention comprises rotary reflectors 308, 310 which are positioned about rotatable shaft 308 at different angular orientations relative thereto.

The rotary reflectors 308, 310 are, preferably, positionable in a plurality of positions relative to the first and second output waveguides 314, 316 of the 3 dB waveguide hybrid junction 302 by rotation of the rotatable shaft 304. In a first exemplary position illustrated in FIGS. 3B and 3C, planes 338, 340 of the rotary reflectors 308, 310 define an azimuth angle, $\Theta_1$, relative to planes 342, 344 of the first and second output waveguides 314, 316 which measures zero (i.e., planes 338, 340, 342, 344 are all coplanar). In a second exemplary position illustrated in the schematic partial cross-sectional views of FIGS. 3D and 3E respectively taken along lines 3D-3D and 3E-3E of FIG. 3A, planes 338, 340 of the rotary reflectors 308, 310 define an azimuth angle, $\Theta_2$, relative to planes 342, 344 of the first and second output waveguides 314, 316 which measures ninety degrees (i.e., planes 338, 340 are, respectively, perpendicular to planes 342, 344).

In operation, the phase angle, $\phi$, of the phase shifted RF waves of a pulse of phase shifted RF waves output by the high-speed phase shifter 300 depends on the orientation of the rotary reflectors 308, 310 relative to the first and second output waveguides 314, 316 of the 3 dB waveguide hybrid junction 302 (and, hence, on their azimuth angle, $\Theta$, relative to planes 342, 344 of the first and second output waveguides 314, 316 of the 3 dB waveguide hybrid junction 302). Therefore, by rotating the rotary reflectors 308, 310 between desired positions thereof (and, hence, between different azimuth angles $\Theta$) at a rate substantially equal to the rate at which pulses of RF waves are received by the input waveguide 312, the phase angle, $\phi$, of the phase shifted RF waves of a pulse of phase shifted RF waves output by the high-speed phase shifter 300 is changed accordingly.

Figure 4:
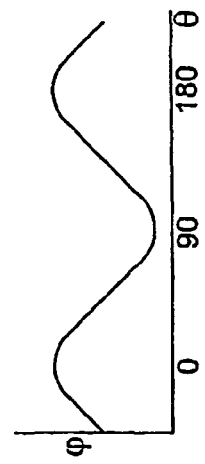
FIG. 4 displays a graphical illustration of the relationship between the phase angle, p, of RF waves output by a high-speed phase shifter and the azimuth angle, 8, of rotary reflectors thereof.

FIG. 4 displays a graphical illustration of this relationship between the phase angle, $\phi$, of the phase shifted RF waves of a pulse of phase shifted RF waves output by the high-speed phase shifter 300 and the azimuth angle, $\theta$, of the rotary reflectors 308, 310 relative to planes 342, 344 of the first and second output waveguides 314, 316. As illustrated in FIG. 4, when the rotary reflectors 308, 310 are rotated into the first position described above to change the phase of the received RF waves, the phase angle, $\phi$, of the phase shifted RF waves of a pulse of phase shifted RF waves output by the high-speed phase shifter 300 is at a maximum value. When the rotary reflectors 308, 310 are rotated into the second position described above to change the phase of the received RF waves, the phase angle, $\phi$, of the phase shifted RF waves of a pulse of phase shifted RF waves output by the high-speed phase shifter 300 is a different phase angle, $\phi$, which, in such case, is a minimum phase angle. Because the rotary reflectors 308, 310 are rotatable into a plurality of positions thereof at a rate substantially equal to and synchronized with the rate at which pulses of charged particles are emitted by injector 108 and pulses of RF waves are received by input waveguide 312, the high-speed phase shifter 300 is operable to produce pulses of output phase shifted RF waves having a desired phase angle, $\phi$, at a rate required by the particle accelerator system 100 for changing of the accelerating field of the second accelerating section 104 thereof according to whether a high energy pulse of charged particles or a low energy pulse of charged particles is presently being generated by the particle accelerator system 100 (i.e., according to whether the particle accelerator system 100 is operating in a high energy mode or in a low energy mode).

In accordance with the first embodiment of the present invention described herein, the rotary reflectors 308, 310 are rotated about longitudinal axis 306 at a rotation rate of 50 Hz. However, it should be understood that the scope of the present invention comprises a high-speed phase shifter 300 having rotary reflectors 308, 310 which are rotatable at different rotation rates to change the phase angle, $\phi$, of the output phase shifted RF waves as appropriate.

Figure 5:
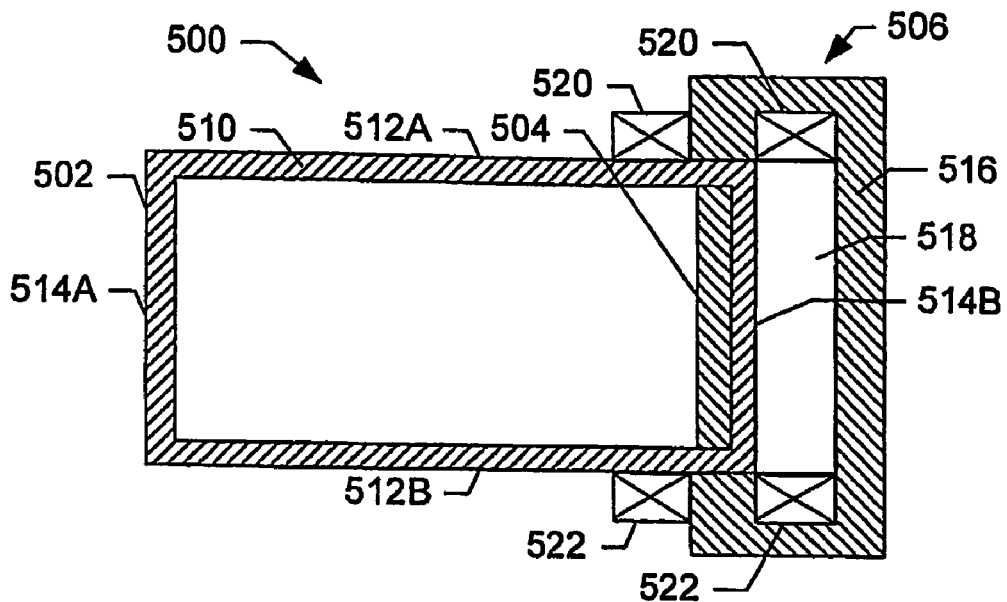
FIG. 5 displays a schematic cross-sectional view of a third form of a high-speed phase shifter taken perpendicular to a longitudinal axis thereof, which is employable as a phase shifter in accordance with the first and second embodiments of the present invention.

FIG. 5 displays a schematic cross-sectional view of a third form of a high-speed phase shifter 500 taken perpendicular to a longitudinal axis thereof, which is employable as a phase shifter 134 in accordance with the first embodiment of the present invention. High-speed phase shifter 500 comprises a waveguide segment 502, a ferrite element 504 positioned within the waveguide segment 502, and an electromagnet 506 that is secured to the outside of the waveguide segment 502. The waveguide segment 502 has a first end (not shown) that is connectable to an external waveguide for the receipt of pulses of input RF waves there from. The waveguide segment 502 also has a second end (not shown) that is connectable to an external waveguide for the output of pulses of phase shifted RF waves produced by the high-speed phase shifter 500. Additionally, the waveguide segment 502 has wall 510 that defines the substantially rectangular cross-section thereof such that the waveguide segment 502 includes opposing wide sides 512A, 512B and opposing narrow sides 514A, 514B.

The electromagnet 506 is secured to the outside of waveguide segment 502 proximate narrow side 514B and comprises a core 516 defining a hollow cavity 518 therein adjacent narrow side 514B. The electromagnet 506 further comprises a first coil 520 and a second coil 522. Coil 520 extends substantially around a portion of core 516 at a first end thereof. coil 522 similarly extends substantially around a second portion of core 516 at a second end thereof. The first and second coils 520, 522 are operable to create a magnetic field in the ferrite element 504 which is located inside the waveguide segment 502 at a position adjacent an inner surface of wall 510 proximate to narrow side 514B of the waveguide segment 502.

In operation, the first and second coils 520, 522 are energized to create a magnetic field in the ferrite element 504. The phase of the phase shifted RF waves of a pulse of phase shifted RF waves output by the high-speed phase shifter 500 is changed by altering the magnetic field created in the ferrite element 504 through appropriate energizing and/or de-energizing of the first and second coils 520, 522. Because the magnetic field created in the ferrite element 502 by the first and second coils 520, 522 is changeable at a rate substantially equal to and synchronized with the rate at which pulses of charged particles are emitted by injector 108 and pulses of RF waves are received by waveguide segment 502, the high-speed phase shifter 500 is operable to produce pulses of output phase shifted RF waves having a desired phase angle, $\phi$, at a rate required by the particle accelerator system 100 for changing of the accelerating field of the second accelerating section 104 thereof according to whether a high energy pulse of charged particles or a low energy pulse of charged particles is presently being generated by the particle accelerator system 100 (i.e., according to whether the particle accelerator system 100 is operating in a high energy mode or in a low energy mode).

Figure 6A:
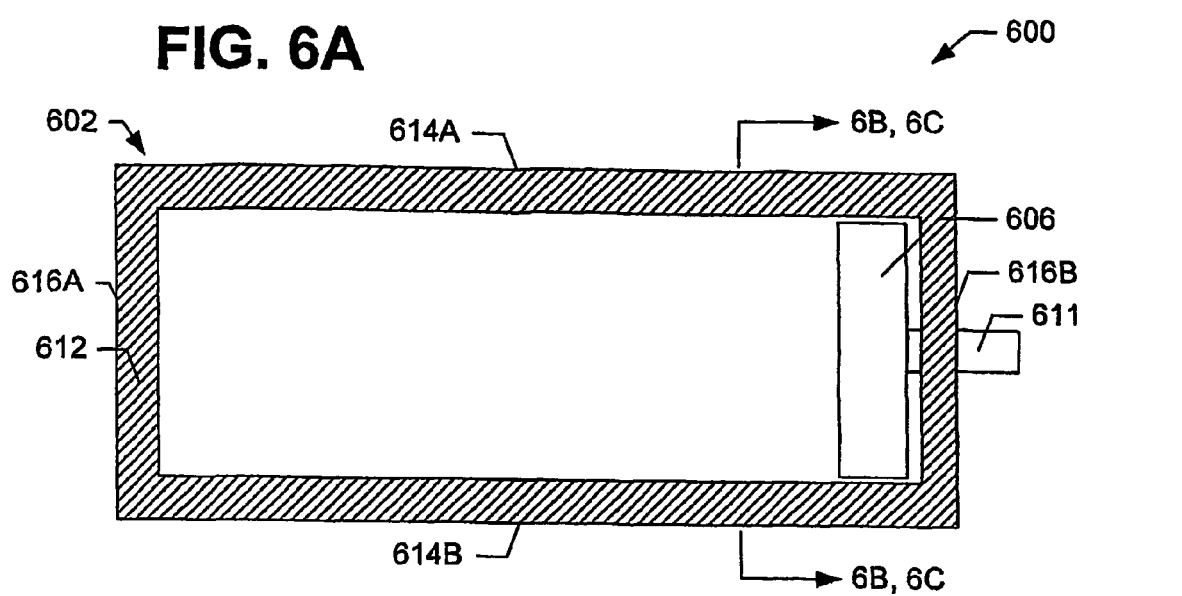
FIG. 6A displays a schematic cross-sectional view of a fourth form of a high-speed phase shifter taken perpendicular to a longitudinal axis thereof, which is employable as a phase shifter in accordance with the first and second embodiments of the present invention.

FIG. 6A displays a schematic cross-sectional view of a fourth form of a high-speed phase shifter 600 taken perpendicular to a longitudinal axis thereof, which is employable as a phase shifter 134 in accordance with the first embodiment of the present invention. High speed phase shifter 600 comprises a waveguide segment 602 and two rotary asymmetric reflectors 604, 606 (also sometimes referred to herein as "rotary reflectors 604, 606"). The waveguide segment 602 has a first end 608 (see FIGS. 6B and 6C) that is connectable to an external waveguide for the receipt of pulses of input RF waves therefrom. The waveguide segment 602 also has a second end 609 that is connectable to an external waveguide for the output of pulses of phase shifted RF waves produced by the high-speed phase shifter 600. Additionally, the waveguide segment 602 has wall 612 that defines the substantially rectangular cross-section thereof such that the waveguide segment 602 includes opposing wide sides 614A, 614B and opposing narrow sides 616A, 616B.

The rotary reflectors 604, 606 are located substantially adjacent to the inner surface of wall 612 proximate narrow side 616B of the waveguide segment 602. Preferably, the rotary reflectors 604, 606 are manufactured from a dielectric material or other material having similar properties. The rotary reflectors 604, 606 are secured to respective rotatable shafts 610, 611 having respective longitudinal axes 618, 620. The rotatable shafts 610, 611 extend through wall 612 at the narrow side 616B of the waveguide segment 602 and are operable for rotation at an appropriate rate and/or at appropriate times by an suitable drive system (not shown) such that when rotatable shafts 610, 611 are rotated about their respective longitudinal axes 618, 620, the rotary reflectors 604, 606 are also rotated about longitudinal axes 618, 620. Preferably, the rotatable shafts 610, 611 are rotated in unison, in the same angular direction, at the same rate, and/or at the same times, thereby causing the rotary reflectors 604, 606 to also be rotated in unison, in the same angular direction, at the same rate, and/or at the same times.

Figure 6B:
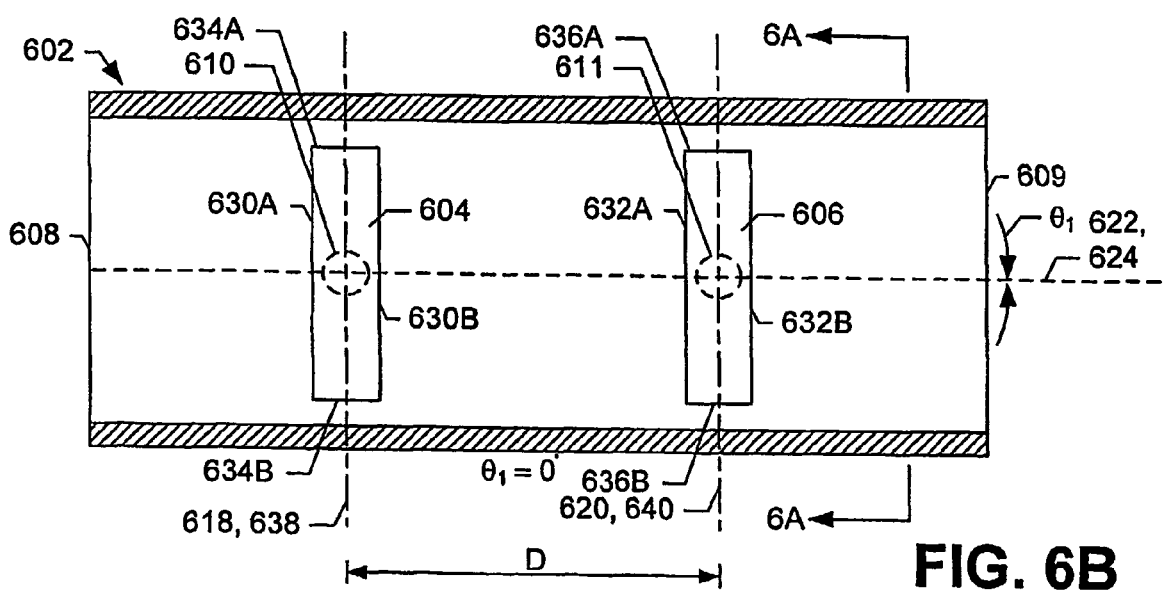
FIG. 6B displays a schematic cross-sectional view of the fourth form of a high-speed phase shifter taken along lines 6B-6B of FIG. 6A.
Figure 6C:
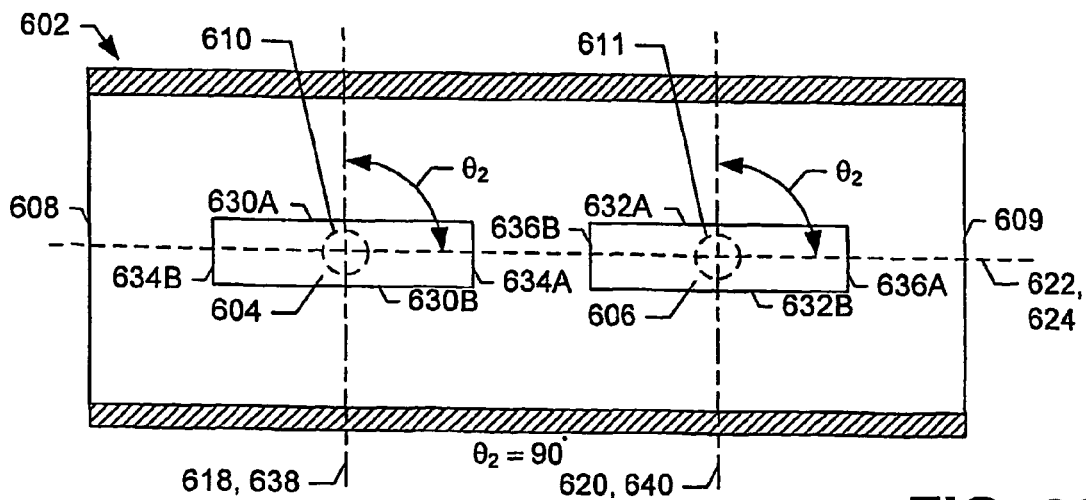
FIG. 6C displays a schematic cross-sectional view of the fourth form of a high-speed phase shifter taken along lines 6C-6C of FIG. 6A.

As illustrated in the schematic cross-sectional views of FIGS. 6B and 6C which are taken along lines 6B-6B and 6C-6C of FIG. 6A, the first rotary reflector 604 is, preferably, located relative to the second reflector 606 such that the distance, D, between the respective longitudinal axes 618, 620 about which the rotary reflectors 604, 606 rotate is equal to one fourth of the waveguide segment's wavelength. By locating the first rotary reflector 604 relative to the second rotary reflector 606 at such a distance, D, reflections from the rotary reflectors 604, 606 are compensated for. As also illustrated in FIGS. 6B and 6C, reference planes 622, 624 are defined as passing through the respective longitudinal axes 618, 620 of rotary reflectors 604, 606 and are oriented perpendicular to the wide sides 614A, 614B of waveguide segment 602 and parallel to the first and second ends 608, 610 thereof.

The rotary reflectors 604, 606, preferably, comprise rectangular-shaped plates having rectangular-shaped cross-sections with holes 626, 628 extending therethrough for receipt of respective rotatable shafts 610, 611. The dimensions of the rotary reflectors 604, 606 are selected to enable the rotary reflectors 604, 606 to be freely rotated adjacent to the inner surface of wall 612 proximate narrow side 616B of the waveguide segment 60 upon rotation of rotatable shafts 610, 611. It should be understood that the scope of the present invention comprises rotary reflectors 604, 606 of different forms having different shaped cross-sections and which are manufactured wholly, or in part, from different materials.

The rotary reflectors 604, 606, as illustrated in FIGS. 6B and 6C, have respective opposing long sides 630A, 630B, 632A, 632B and respective opposing short sides 634A, 634B, 636A, 636B. The rotary reflectors 604, 606 are, preferably, positioned about rotatable shafts 610, 611 at the same angular orientation relative thereto such that rotary reflector 604 is hidden behind rotary reflector 606 in FIG. 6A. Reference planes 638, 640 extend through the respective longitudinal axes 618, 620 of rotatable shafts 610, 611 and are, respectively, parallel to the opposing long sides 630A, 630B, 632A, 632B of the rotary reflectors 604, 606. It should be understood that the scope of the present invention comprises rotary reflectors 604, 606 which are positioned about rotatable shafts 610, 611 at different angular orientations relative thereto.

The rotary reflectors 604, 606 are, preferably, positionable in a plurality of positions relative to the waveguide segment 602 by rotation of the rotatable shafts 610, 611. In a first exemplary position illustrated in FIG. 6B, planes 638, 640 of the rotary reflectors 604, 606 define an azimuth angle, $\theta_1$, relative to planes 622, 624 of waveguide segment 602 which measures zero (i.e., planes 638, 640, 622, 624 are all coplanar). In a second exemplary position illustrated in FIG. 6C, planes 638, 640 of the rotary reflectors 604, 606 define an azimuth angle, $\theta_2$, relative to planes 622, 624 of waveguide segment 602 which measures ninety degrees (i.e., planes 638, 640 are, respectively, perpendicular to planes 622, 624).

In operation, the phase angle, $\phi$, of the phase shifted RF waves of a pulse of phase shifted RF waves output by the high-speed phase shifter 600 depends on the orientation of the rotary reflectors 604, 606 relative to the waveguide segment 602 (and, hence, on their azimuth angle, $\theta$, relative to planes 622, 624 of waveguide segment 602). Therefore, by rotating the rotary reflectors 604, 606 between desired positions thereof (and, hence, between different azimuth angles θ) at a rate substantially equal to the rate at which pulses of RF waves are received by the waveguide segment 602, the phase angle, φ, of the phase shifted RF waves of a pulse of phase shifted RE waves output by the high-speed phase shifter 600 is changed accordingly.

The relationship between the phase angle, φ, of the phase shifted RF waves of a pulse of phase shifted RF waves output by the high-speed phase shifter 600 and the azimuth angle, θ, of the rotary reflectors 604, 606 relative to planes 622, 624 of the waveguide segment 602 is substantially similar to that illustrated in FIG. 4 and described above with respect to high speed phase shifter 300. As illustrated in FIG. 4 and with respect to high-speed phase shifter 600, when the rotary reflectors 604, 606 are rotated into the first position described above to change the phase of the received RF waves, the phase angle, φ, of the phase shifted RF waves of a pulse of phase shifted RF waves output by the high-speed phase shifter 600 is at a maximum value. When the rotary reflectors 604, 606 are rotated into the second position described above to change the phase of the received RF waves, the phase angle, φ, of the phase shifted RF waves of a pulse of phase shifted RF waves output by the high-speed phase shifter 600 is a different phase angle, φ, which, in such case, is a minimum phase angle. Because the rotary reflectors 604, 606 are rotatable into a plurality of positions thereof at a rate substantially equal to and synchronized with the rate at which pulses of charged particles are emitted by injector 108 and pulses of RF waves are received by waveguide segment 602, the high-speed phase shifter 600 is operable to produce pulses of output phase shifted RF waves having a desired phase angle, φ, at a rate required by the particle accelerator system 100 for changing of the accelerating field of the second accelerating section 104 thereof according to whether a high energy pulse of charged particles or a low energy pulse of charged particles is presently being generated by the particle accelerator system 100 (i.e., according to whether the particle accelerator system 100 is operating in a high energy mode or in a low energy mode).

It should be understood that while high-speed phase shifter 600 has been described herein as comprising two rotary reflectors 604, 606, it should be understood that the scope of the present invention comprises similar high-speed phase shifters having one or more rotary reflectors. It should be understood that while the rotary reflectors 604, 606 of high-speed phase shifter 600 are, generally, rotated in unison by respective rotatable shafts 610, 611 and oriented in the same position relative to respective reference planes 622, 624 at a particular time, the scope of the present invention comprises similar high-speed phase shifters having rotary reflectors which are not rotated in unison by respective rotatable shafts and/or which are not oriented in the same position relative to respective reference planes 622, 624 at such particular time.

Figure 7:
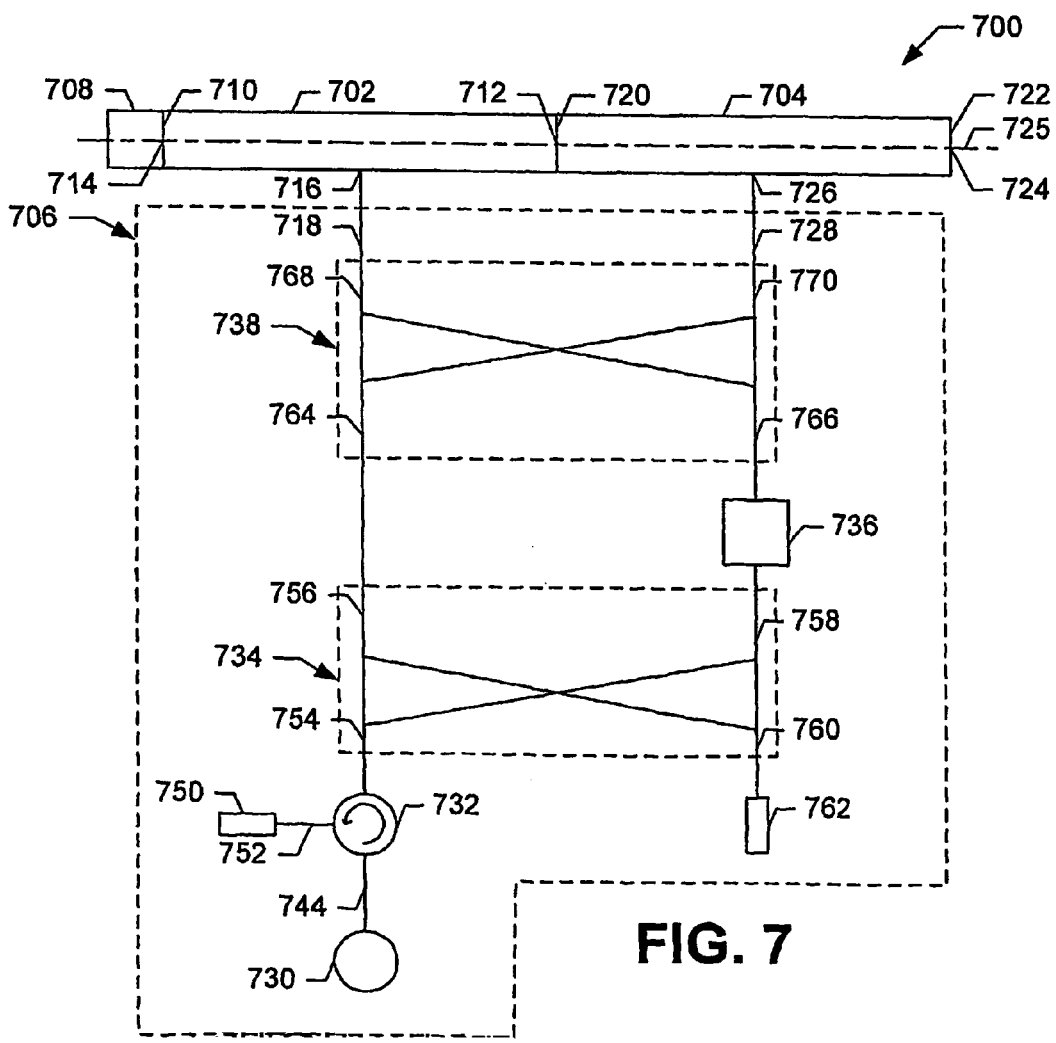
FIG. 7 displays a schematic block diagram representation of a particle accelerator system in accordance with a second embodiment of the present invention.

FIG. 7 displays a schematic block diagram representation of a particle accelerator system 700 in accordance with a second embodiment of the present invention. The particle accelerator system 700 comprises a first accelerating section 702, a second accelerating section 704, an RF drive subsystem 706, and an injector 708. In the second embodiment, the first and second accelerating sections 702, 704 and the injector 708 are substantially similar to the first and second accelerating sections 102, 104 and the injector 108 of the first embodiment.

The first accelerating section 702 has a first end 710 and a second end 712. The injector 708 is positioned proximate the first end 710 of the first accelerating section 702 and is connected to an input port 714 of the first accelerating section 702. The injector 708 is operable to generate charged particles and to emit them in a pulsed mode of operation as pulses of charged particles, into the first accelerating section 702 through input port 714. The rate at which the injector 708 emits pulses of charged particles may be increase or decreased as needed. The first accelerating section 702 defines an oblong-shaped slot 716 that couples the first accelerating section 702 to a feeder waveguide 718 of the RF drive subsystem 706 to enable RF power to propagate from the feeder waveguide 718 into and through the first accelerating section 702.

Similar to the first accelerating section 702, the second accelerating section 704 has a first end 720 and a second end 722. The second accelerating section 704 is appropriately connected to the first accelerating section 702 to enable charged particles to travel between the first and second accelerating sections 702, 704. The second accelerating section 704 includes an output port 724 located at the second end 722 of the second accelerating section 704. A longitudinal axis 725 of the particle accelerating system 100 extends between, and is defined by, the input port 714 and the output port 724. The output port 724 is adapted to direct a beam of charged particles from the second accelerating section 702 (and, hence, from the particle accelerator system 700) toward a desired target or other object. The second accelerating section 704 defines an oblong-shaped slot 726 which couples the second accelerating section 704 to a feeder waveguide 728 of the RF drive subsystem 706 to allow RF power to propagate from the feeder waveguide 728 into and through the second accelerating section 704.

The RF drive subsystem 706 comprises an RF source 730, an isolating device 732, a 25 first 3 dB waveguide hybrid junction 734, a phase shifter 736, and a second 3 dB waveguide hybrid junction 738. The RF source 730 is operable to generate RF power in the form of pulses of RF waves, having an appropriate frequency, power level, and pulse repetition rate, using a pulsed mode of operation synchronized with the emission of charged particles by injector 708 and to output such RF power via connected waveguide 744. Preferably, the RF source 730 includes a magnetron which generates 2.5 MW of RF power in the form of pulses of RF waves having a frequency of 2.8 0 Hz and a pulse repetition rate of 200 Hz. Also preferably, the RF source 730 may include a microwave generator, klystron, or other device for generating an appropriate level of RF power in the form of pulses of RF waves having an appropriate frequency and pulse repetition rate.

An isolating device 732 is connected to the RF source 730, via waveguide 744, for receiving RF power and pulses of RF waves generated and output by RF source 730. The isolating device 732 is operable to prevent RF power from propagating back to and reentering RF source 730, and thereby possibly damaging the RF source 730. The isolating device 732 is connected to a waveguide load 750 via waveguide 752. Waveguide load 750 is operable to dissipate reflected RF power received from connected waveguide 754. Preferably, the isolating device 732 comprises a ferrite circulator or a ferrite isolator. It should be understood that the scope of the present invention includes other appropriate devices for isolating an RF source 730.

Isolating device 732 is also connected to an input waveguide 754 of a first 3 dB waveguide hybrid junction 734 and is adapted to receive RF power in the form of pulses of RF waves supplied from the RF source 730 via the isolating device 732. The first 3 dB waveguide hybrid junction 734 has an input waveguide 754 and three output waveguides 756, 758, 760. Output waveguides 756, 758 are adapted to receive generated RF power from input waveguide 754 and to deliver it, respectively, to waveguide 764 of a second 3 dB waveguide hybrid junction 738 and phase shifter 736. Output waveguide 760 connects to a matched waveguide load 762. The matched waveguide load 762 is adapted to receive and dissipate reflected RE power.

Output waveguide 758, as indicated above, connects to phase shifter 736, which is substantially similar to the phase shifter 134 of the first embodiment and is, therefore, not described again in detail. Phase shifter 736 is capable of shifting the phase of the RF waves of a received pulse of RF waves between at least a first and a second phase and doing so in synchronization with pulses of charged particles emitted by injector 108. Phase shifter 736, preferably, comprises one of the high-speed phase shifters 200, 300, 500, 600 described with reference to FIGS. 2, 3, 5, and 6 below. It should be understood that the scope of this invention includes other appropriate devices capable of shifting the phase of the RF waves of a pulse of RF waves between first and second phases that are appropriate.

Output waveguide 756 connects to input waveguide 764 of second 3 dB waveguide hybrid junction 738. The second 3 dB waveguide hybrid junction 738 has two input waveguides 764, 766 and two output waveguides 768, 770. The second input waveguide 766 is connected to a waveguide of the phase shifter 736 and is adapted to receive a pulse of phase shifted RF waves from the phase shifter 736. Output waveguide 768 connects to the input waveguides 764, 766 and is adapted to receive RF power in the form of pulses of RF waves from input waveguide 764 and RF power in the form of pulses of phase shifted RF waves from input waveguide 766 and to supply such RF power to the first accelerating section 702 through connected feeder waveguide 718 and oblong-shaped slot 116 thereof so as to create an accelerating field in the first accelerating section 702. Similarly, output waveguide 770 connects to the input waveguides 764, 766 and is adapted to receive generated RF power in the form of pulses of RF waves from input waveguide 764 and RF power in the form of pulses of phase shifted RF waves from input waveguide 766 and to supply such RF power to the second accelerating section 704 through connected feeder waveguide 728 an oblong-shaped slot 726 thereof so as to create an accelerating field in the second accelerating section 704. Together the first 3 dB waveguide hybrid junction 734, the phase shifter 736, and the second 3 dB waveguide hybrid junction 738 function as a variable, directional coupler to regulate the ratio of the RF power supplied to the first and second accelerating sections 702, 704.

In operation, the injector 708 of the particle accelerating system 700 generates and emits charged particles (preferably, electrons) into the first accelerating section 702 and, concurrently, the RF source 730 of the RF drive subsystem 706 generates RF power, in a pulsed mode of operation synchronized with the emission of charged particles by injector 708, and outputs such RF power in the form of pulses of RF waves. The RF source 730 delivers such RF power to isolating device 732 via waveguide 744. The isolating device 732 prevents the generated RF power from returning to the RF source 730. Reflections of the RF power are directed by the isolating device 732, via waveguide 752, to the waveguide load 750, where the RF power is dissipated.

From the isolating device 732, the generated RF power enters the input waveguide 754 of the first 3 dB waveguide hybrid junction 734. The first 3 dB waveguide hybrid junction 734 divides the RF power (preferably, in half) with a first portion of the generated RF power propagating through output waveguide 756 of the 3 dB waveguide hybrid junction 734 and into the first input waveguide 764 of the second 3 dB waveguide hybrid junction 738.

A second portion of the generated RF power propagates through output waveguide 758 of the first 3 dB waveguide hybrid junction 734 and into phase shifter 736. The phase of the RF waves in the pulses of RF waves is, preferably, changed by phase shifter 736 using the appropriate operating method of high-speed phase shifters 200, 300, 500, 600 employed as phase shifter 736, as described in detail above. Alternatively, the phase of the RF waves in the pulses of RF waves of the generated RF power may be changed by other appropriate devices and methods.

The phase shifted RF powers (i.e., in the form of pulses of phase shifted RF waves) then propagate through phase shifter 736 and into the second input waveguide 766 of the second 3 dB waveguide hybrid junction 738. The phase shifted RF power is then divided by the second 3 dB waveguide hybrid junction 738, into first and second portions of the phase shifted RF power with, preferably, the first portion of the phase shifted RF power (i.e., one-fourth of the generated RF power) propagating via output waveguide 768 into feeder waveguide 718. Subsequently, the first portion of the phase shifted RF power propagates into and throughout the first accelerating section 702 via oblong-shaped slot 716. The second portion of the phase shifted RF power (i.e., one-fourth of the generated RF power) propagates via output waveguide 770 into feeder waveguide 728. Subsequently, the second portion of the phase shifted RF power propagates into and throughout the second accelerating section 704 via oblong-shaped slot 726.

The generated RF power from waveguide 756 is then divided by the second 3 dB waveguide hybrid junction 738 into first and second portions of the generated RF power with, preferably, the first portion of the RF power (i.e., preferably, one-fourth of the generated RF power) propagating, via output waveguide 768, into feeder waveguide 718. Subsequently, the first portion of the RF power propagates into and throughout the first accelerating section 702 via oblong-shaped slot 716. The second portion of the RF power (i.e., preferably, one-fourth of the generated RF power) propagates, via output waveguide 770, into feeder waveguide 728. Subsequently, the second portion of the RF power propagates into and throughout the first accelerating section 704 via oblong-shaped slot 726.

Consequently, the RF waves having amplitudes corresponding to one-fourth of the generated power with and without phase shift propagate into and throughout each of the accelerating sections 702, 704. Contemporaneously, the charged particles emitted into the first accelerating section 702 travel through the first accelerating section 702 while being accelerated by the accelerating field developed from the RF waves having amplitudes corresponding to one-fourth of the generated power with and without phase shift and formed into a charged particle beam. Upon reaching the second end 712 of the first accelerating section 702, the charged particles of the charged particle beam travel into and through the second accelerating section 704 while being further accelerated by the accelerating field developed from the RF waves having amplitudes corresponding to one-fourth of the generated power with and without phase shift. The charged particles of the charged particle beam exit the particle accelerator system 700 via output port 724 located at the second end 722 thereof as pulses of bunched charged particles (preferably, electrons).

It should be noted that although the 3 dB waveguide hybrid junctions 734, 738 have been described as dividing the generated RF power equally between the output waveguides 756, 758 and 768, 770, respectively, the 3 dB waveguide hybrid junctions 734, 738 are capable of dividing the RF power in any ratio. It should also be noted that the phase differential of the RF waves of the pulses of RF waves in output waveguides 768, 770 does not depend on the configuration of the phase shifter 736. However, the amplitude of the RF waves in the pulses of RF waves depends on the phase shift performed by the phase shifter 736. Additionally, it should be noted that the RF power in the output waveguides 768, 770 is proportional to the electromagnetic field amplitude, E, squared. At the output feeder waveguides 718, 728 of the second 3 dB waveguide hybrid junction 738, the electromagnetic fields of the RF waves having amplitudes corresponding to one-fourth of the generated power with and without phase shift in the feeder waveguide 718 and the electromagnetic fields of the RF waves having amplitudes corresponding to one-fourth of the generated power with and without phase shift in the feeder waveguide 728 are summed vectorially by taking into account their the phase differentials. For example, in one extreme mode, if the phase shifter 736 is configured such that at the junction of the output feeder waveguides 718, 728 of the second 3 dB waveguide hybrid waveguide junction 738 the phases of the each of the RF waves having amplitudes corresponding to one-fourth of the generated power with and without phase shift in the feeder waveguide 718 and the electromagnetic fields of the RF waves having amplitudes corresponding to one-fourth of the generated power with and without phase shift in the feeder waveguide 728 coincide, the sum of the amplitudes of the RF waves is taken. Thus, the entire RF power propagates through output feeder waveguide 718 through oblong-shaped slot 716 and into the first accelerating section 702, and none of the RF power enters the second accelerating section 704.

To further illustrate this example, the following equation represents the electromagnetic field created in the waveguide at the input of first accelerating section 702, "E," as defined by the relationship between the amplitudes of the electromagnetic fields in output feeder waveguides 718, 728 and the phase of the phase shifted RF wave:

$$E = \sqrt{E_1^2 + E_2^2 + 2 \cdot E_1 \cdot E_2 \cdot \cos\phi}.$$

where $E_1$ and $E_2$ are amplitudes of the electromagnetic fields of RF waves having amplitudes corresponding to one-fourth of the generated power with and without phase shift in the output feeder waveguides 718, 728 and $\phi$ is the phase shift between these RF waves. Where both 3 dB waveguide hybrid junctions 734, 738 divide the RF waves equally, $E_1$ equals $E_2$. In this mode, where the RF waves are equally divided between the first and second accelerating sections 702, 704, $\phi$ equals ninety degrees. However, in the extreme mode previously described above where the entire generated RF power is directed into the first accelerating section 702, and no proportion of the RF power is directed into the second accelerating section 704, $\phi$ equals zero degrees. Thus, the change of the phase shift in the phase shifter 736 allows control of power division and delivery between the first accelerating section 702 and the second accelerating section 704 from (i) the entire RF power being delivered to the first accelerating section 702 and no RF power being delivered to the second accelerating section 704 to (ii) no RF power being delivered to the first accelerating section 702 and the entire RF power being delivered to the second accelerating section 704.

Preferably, the particle accelerating system 700 alternately operates in two modes, a high energy mode and a low energy mode in which the high and low energy modes alternate between successive pulses such that the pulses generated and output by the particle accelerating system 700 alternately have high and low energy levels. In the high energy mode of operation, the phase shift of the RF power performed by phase shifter 736 is selected such that the accelerating fields created in the first and second accelerating sections 702, 704 are approximately equal in strength.

In the low energy mode of operation, the phase shift of the RF power performed by the phase shifter 736 is selected to increase the strength of the accelerating field created in the first accelerating section 702 relative to the strength of the accelerating field created in the second accelerating section 704. To compensate for the increased strength of the accelerating field in the first accelerating section 702, the rate at which the injector 708 emits charged particles into the first accelerating section 702 (i.e., the injector current) is increased. By increasing the current, the strength of the accelerating field created in the first accelerating section 702 in the low energy mode equals the strength of the accelerating field created in the first accelerating section 702 in the high energy mode. As a consequence, the incremental change in the energy level of each charged particle in the first accelerating section 702 is identical in both the high energy and the low energy modes.

However, in the low energy mode, the strength of the accelerating field in the second accelerating section 704 is reduced relative to the strength of the accelerating field in the second accelerating section 704 in the high energy mode. Thus, in the low energy mode, the incremental change in the energy level of the charged particles in the second accelerating section 704 is smaller relative to the incremental change in the energy level of the charged particles in the second accelerating section 704 in the high energy mode.

Figure 8:
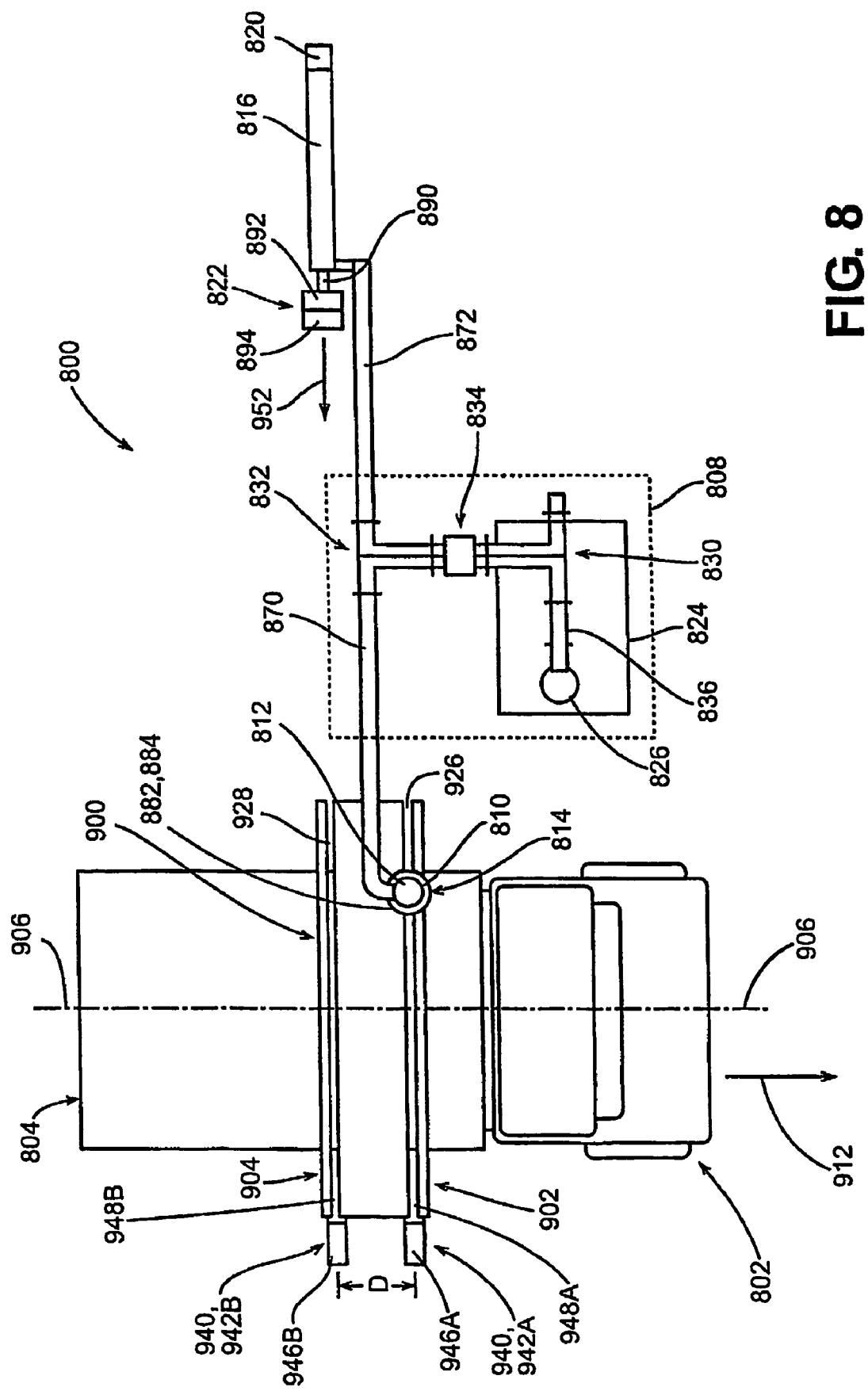
FIG. 8 displays a top, plan pictorial view of a radiographic inspection system, in accordance with a third embodiment of the present invention, for producing images of the contents of a vehicle and/or a cargo container viewed from multiple directions and in multiple planes, and for the discrimination of materials present in the contents thereof.

FIG. 8 displays a top, plan pictorial view of a radiographic inspection system 800, in accordance with a third embodiment of the present invention, for producing images of the contents of a vehicle 802 and/or a cargo container 804 viewed from multiple directions and in multiple planes, and the discrimination of materials present in the contents that may utilize the various forms of phase shifters described above. The vehicle 802 and cargo container 804 may be independently inspected alone or together, as illustrated in FIG. 8, where the vehicle 802 comprises a flat bed truck and the cargo container 804 is secured thereto. Generally, the radiographic inspection system 800 of the third embodiment is configured to inspect vehicles 802 and/or cargo containers 804 having an approximately 2.5×2.5 meter frontal cross-sectional area. It should be understood, however, that the radiographic inspection system 800 may be adapted, as necessary, to produce images of vehicles 802 and/or cargo containers 804 having different frontal cross-sectional areas.

The radiographic inspection system 800 is adapted to irradiate the vehicle 802 and/or cargo container 804 with pulses of alternating high and low energy radiation impinging thereon from multiple directions and in corresponding multiple planes. The radiographic inspection system 800 comprises a single RF drive subsystem 808, a first accelerating section 810, a first injector 812, a first radiation field forming device 814, a second accelerating section 816, a second injector 820, and a second radiation field forming device 822. The RF drive subsystem 808, importantly, includes a single power supply 824 and a single RF source 826 that connects to an output of the power supply 824 for the receipt of power therefrom. The RF source 826 is operable to generate RF power in the form of pulses of RF waves, having an appropriate frequency, power level, and pulse repetition rate, using a pulsed mode of operation synchronized with the emission of charged particles by first and second injectors 812, 820. In a form acceptable in accordance with the third embodiment, the RF source 826 comprises a klystron operating in the S-band frequency range and rated at 5 MW pulse (peak) power and 10 kW maximal average power. The first and second accelerating sections 810, 816, in such acceptable form, comprise 9 MeV electron accelerating sections of approximately one meter in length that use bi-periodic standing wave accelerating structures and produce electron beams each having beam pulse currents of approximately 0.18 A. In other forms acceptable in accordance with the third embodiment, the RF source 826 may include a microwave generator, magnetron, or other device for generating an appropriate level of RF power in the form of pulses of RF waves having an appropriate frequency and pulse repetition rate.

The RF drive subsystem 808 also includes a first 3 dB waveguide hybrid junction 830, a second 3 dB waveguide hybrid junction 832, a phase shifter 834 that connects between the first and second 3 dB waveguide hybrid junctions 830, 832, a waveguide load 836, and an isolating device 838. The first and second 3 dB waveguide hybrid junctions 830, 832 are, generally, formed from two parallel waveguides with each 3 dB waveguide hybrid junction 830, 832 having a coupling window in a common shared wall thereof to enable the passage of RF power between the two parallel waveguides. Together, the first 3 dB waveguide hybrid junction 830, second 3 dB waveguide hybrid junction 832, and phase shifter 834 function as a controlled, variable, directional coupler to regulate the ratio of the RF power supplied to the first and second accelerating sections 810, 816 using any coefficient of transient attenuation.

The first 3 dB waveguide hybrid junction 830, as illustrated in FIG. 9, has an input waveguide 850 and first, second, and third output waveguides 852, 854, 856. The second 3 dB waveguide hybrid junction 832 has input waveguides 860, 862 and output waveguides 864, 866. The input waveguide 850 of the first 3 dB waveguide hybrid junction 830 connects to the RF source 826 via isolating device 838 for the receipt of RF power from the RF source 826. The first and second output waveguides 852, 854 of the first 3 dB waveguide hybrid junction 830 connect, respectively, to the input waveguides 860, 862 of the second 3 dB waveguide hybrid junction 832 via the phase shifter 834, for the delivery of RF power from the input waveguide 850 of the first 3 dB waveguide hybrid junction 830 to the second 3 dB waveguide hybrid junction 832. The third output waveguide 856 of the first 3 dB waveguide hybrid junction 830 connects to the waveguide load 836. The first and second output waveguides 864, 866 of the second 3 dB waveguide hybrid junction 830 connect to respective feeder waveguides 870, 872 that connect, respectively, to the first and second accelerating sections 810, 816 for the delivery of RF power from the RF drive subsystem 808 to the first and second accelerating sections 810, 816.

The isolating device 838 is configured to receive RF power and pulses of RF waves generated and output by the RF source 826 and to deliver the RF power to the input waveguide 850 of the first 3 dB waveguide hybrid junction 830. The isolating device 838 is operable to prevent RF power from propagating back to and reentering the RF source 826, and thereby possibly damaging the RF source 826. Generally, the isolating device 838 comprises a ferrite circulator or ferrite isolator. Similarly, the waveguide load 836 is adapted to dissipate reflected RF power received from the first and second accelerating sections 810, 816 during the transient startup period when the first and second accelerating sections 810, 816 are being filled with RF power. It should be understood that the scope of the present invention includes other appropriate devices for isolating RF source 826.

Phase shifter 834 is substantially similar to the phase shifter 134 of the first embodiment and is, therefore, not described again in detail. Phase shifter 834 is capable of shifting the phase of the RF waves of a received pulse of RF waves between at least a first and second phase and doing so in synchronization with pulses of charged particles emitted by first and second injectors 812, 820. Phase shifter 834, generally, comprises one of the high-speed phase shifters 200, 300, 500, 600 described with reference to FIGS. 2, 3, 5, and 6 above. It should be understood that the scope of the present invention includes other appropriate devices capable of shifting the phase of the RF waves of a pulse of RF waves between first and second phases that are appropriate.

The first accelerating section 810, as illustrated in FIG. 10, has a first end and a second end. At the first end, the first injector 812 connects to an input port of the first accelerating section 810. The first injector 812 is operable to generate charged particles and to emit them in a pulsed mode of operation as pulses of charged particles into the first accelerating section 810 via the input port. The rate at which the first injector 812 emits pulses of charged particles may be increased or decreased as needed. The first accelerating section 810 also connects, proximate its second end, to feeder waveguide 870 for the receipt of RF power in the form of pulses of RF waves from the RF drive subsystem 808. The first accelerating section 810 is adapted to accelerate the charged particles received from the first injector 812 via an electric field created therewithin by the received RF power. The first accelerating section 810 may include a first portion for bunching the received charged particles and a second portion for accelerating the bunched charged particles. The accelerated charged particles exit the first accelerating section 810, generally, as a first charged particle beam having successive pulses of accelerated charged particles. Generally, the charged particles comprise electrons.

The first radiation field forming device 814 is positioned proximate the second end of the first accelerating section 810 and connects to the first accelerating section 810 via a connecting waveguide 880. The first radiation field forming device 814 comprises a radiation conversion target 882 and a collimator 884 positioned substantially adjacent to the radiation conversion target 882. The radiation conversion target 882 is, generally, manufactured from heavy metal such as, for example and not limitation, tungsten and is adapted to convert the successive pulses of the first charged particle beam exiting the first accelerating section 810 into successive pulses of bremsstrahlung. The collimator 884, generally, includes a slot extending therethrough that is configured to receive the successive pulses of bremsstrahlung from the radiation conversion target 882 and produce therefrom narrow, substantially planar, fan-shaped, pulsed bremsstrahlung beam 886. The first radiation field forming device 814 may also comprise a turning device interposed between connecting waveguide 880 and the radiation conversion target 882 to turn the first charged particle beam exiting first accelerating section 810 into an appropriate direction, if necessary.

Similar to the first accelerating section 810, the second accelerating section 816 has a first end and a second end (see FIGS. 8 and 10). At the first end, the second injector 820 connects to an input port of the second accelerating section 816. The second injector 820 is operable to generate charged particles and to emit them in a pulsed mode of operation as pulses of charged particles into the second accelerating section 816 via the input port. The rate at which the second injector 820 emits pulses of charged particles may be increased or decreased as needed. The second accelerating section 816 also connects, proximate its second end, to feeder waveguide 872 for the receipt of RF power in the form of pulses of RF waves from the RF drive subsystem 808. The second accelerating section 816 is adapted to accelerate the charged particles received from the second injector 820 via an electric field created therewithin by the received RF power. The second accelerating section 816 may include a first portion for bunching the received charged particles and a second portion for accelerating the bunched charged particles. The accelerated charged particles exit the second accelerating section 816, generally, as a second charged particle beam having successive pulses of accelerated charged particles. Generally, the charged particles comprise electrons.

The second radiation field forming device 822 is positioned proximate the second end of the second accelerating section 816 and connects to the second accelerating section 816 via a connecting waveguide 890. The second radiation field forming device 822 comprises a radiation conversion target 892 and a collimator 894 positioned substantially adjacent to the radiation conversion target 892. The radiation conversion target 892 is, generally, manufactured from heavy metal such as, for example and not limitation, tungsten and is adapted to convert the successive pulses of the second charged particle beam exiting the second accelerating section 816 into successive pulses of bremsstrahlung. The collimator 894, generally, includes a slot extending therethrough that is configured to receive the successive pulses of bremsstrahlung from the radiation conversion target 892 and produce therefrom narrow, substantially planar, fan-shaped, pulsed bremsstrahlung beam 896. The second radiation field forming device 822 may also comprise a turning device interposed between connecting waveguide 890 and the radiation conversion target 892 to turn the second charged particle beam exiting second accelerating section 816 into an appropriate direction, if necessary.

As illustrated in FIGS. 8 and 10, the radiographic inspection system 800 also comprises an elongate collimator structure 900 having a first end 902 and a second end 904 that define a longitudinal axis 906 extending therebetween. The elongate collimator structure 900 comprises a wall 908 that defines a passageway 910 extending therethrough between first and second ends 902, 904. Generally, the passageway 910 is appropriately sized to enable a vehicle 202 and attached cargo container 204 to travel through the passageway 910 in a direction (i.e., identified by arrow 912) along the longitudinal axis 906 of the collimator structure 900.

The wall 908 has a top portion 914, an opposed bottom portion 916, a first side portion 918 extending between the top and bottom portions 914, 916, and a second side portion 920 opposed to the first side portion 918 and extending between the top and bottom portions 914, 916. The wall 908 has an outer surface 922 and an opposed inner surface 924 extending around passageway 910. The wall 908 defines a first slot 926 that extends between the wall's outer and inner surfaces 922, 924 and through the wall's top, bottom, first side, and second side portions 914, 916, 918, 920. The first slot 926 is substantially planar and is, generally, oriented perpendicular to the elongate collimator structure's longitudinal axis 906. The first slot 926 is configured to further collimate, during operation of the radiographic inspection system 800, the narrow, substantially planar, fan-shaped, pulsed bremsstrahlung beam 886 exiting collimator 884 of the first accelerating section 810.

The wall 908 also defines a second slot 928 offset from the first slot 926 at a distance, "D", measured along the longitudinal axis 906. The second slot 928, substantially similar to the first slot 926, extends between the wall's outer and inner surfaces 922, 924 and through the wall's top, bottom, first side, and second side portions 914, 916, 918, 920. Generally also, the second slot 928 is substantially planar and is oriented perpendicular to the elongate collimator structure's longitudinal axis 906. The second slot 928, similar to the first slot 926, is configured to further collimate, during operation of the radiographic inspection system 800, the narrow, substantially planar, fan-shaped, pulses bremsstrahlung beam 896 exiting collimator 894 of the second accelerating section 816.

The radiographic inspection system 800 additionally comprises, as displayed in FIGS. 8 and 10, a detector 940 having first and second detector arrays 942A, 942B. The detector arrays 942A, 942B each include a plurality of individual detector elements (not visible in FIG. 8 or 10) that are operable to receive bremsstrahlung impinging thereon and to convert the received bremsstrahlung into electrical signals that relate to the intensity of the received bremsstrahlung. Each detector array 942A, 942B has a, generally, "L-shape" with a first portion 946A, 946B extending adjacent to the outer surface 922 of the elongate collimator structure's wall 908 proximate the second side portion 920 thereof and a second portion 948A, 948B extending adjacent to the outer surface 922 of the elongate collimator structure's wall 908 and elevationally beneath the bottom portion 916 thereof. The first detector array 942A is oriented relative to the first slot 926 of the elongate collimator structure's wall 908 such that the first detector array 942A is, generally, coplanar with the first slot 926. The second detector array 942B is, similar to the second slot 928 of the elongate collimator structure's wall 908 relative to the first slot 926 thereof, offset from the first detector array 942A at a distance, "D", measured along the longitudinal axis 906. The second detector array 942B is oriented relative to the second slot 928 of the elongate collimator structure's wall 908 such that the second detector array 942B is, generally, coplanar with the second slot 928.

The first accelerating section 810, in accordance with the third embodiment of the present invention, is located at an appropriate position elevationally offset from and above the top portion 914 of the elongate collimator structure's wall 908 (see FIG. 10). The appropriate position of the first accelerating section 810 is selected such that, during operation of the radiographic inspection system 800, the narrow, substantially planar, fan-shaped, pulsed bremsstrahlung beam 886 exiting collimator 884 passes through the first slot 926 of the elongate collimator structure's wall 908, through the vehicle 202 and cargo container 204 (and, hence, through the contents thereof) in a, generally, downward direction (i.e., indicated in FIG. 10 by arrow 950), and impinges on the first and second portions 946A, 948A of the first detector array 942A. Thus, the planes of the bremsstrahlung beam 886, first slot 926 of the elongate collimator structure's wall 908, and first detector array 942A are, substantially, coplanar and perpendicular to the direction of travel of the vehicle 202 and cargo container 204.

The second accelerating section 816, according to the third embodiment, is located at an appropriate position laterally offset from the first side portion 918 of the elongate collimator structure's wall 908 (see FIGS. 8 and 10). The appropriate position of the second accelerating section 816 is selected such that, during operation of the radiographic inspection system 800, the narrow, substantially planar, fan-shaped, pulsed bremsstrahlung beam 896 exiting collimator 894 passes through the second slot 928 of the elongate collimator structure's wall 908, through the vehicle 202 and cargo container 204 (and, hence, through the contents thereof) in a, generally, lateral direction (i.e., indicated in FIG. 10 by arrow 952), and impinges on the first and second portions 946B, 948B of the second detector array 942B. Thus, the planes of the bremsstrahlung beam 896, second slot 928 of the elongate collimator structure's wall 908, and second detector array 942B are, substantially, coplanar and perpendicular to the direction of travel of the vehicle 202 and cargo container 204.

In operation according to a method of the third embodiment, the first and second injectors 812, 820 generate and emit charged particles (e.g., electrons) into the first and second accelerating sections 810, 816. Concurrently, the RF source 826 of the RF drive subsystem 808 generates RF power, in a pulsed mode of operation synchronized with the emission of charged particles by injectors 812, 820 and outputs such RF power in the form of successive pulses of RF waves to the isolating device 838. The isolating device 838 prevents the generated RF power from returning to the RF source 826. The isolating device 838 also directs any RF power that is reflected by the accelerating sections 810, 816 during the filling thereof with RF power during startup, if any, to the waveguide load 836 via the third output waveguide 856 of the first 3 dB waveguide hybrid junction 830, where any such reflected RF power is dissipated.

From the isolating device 838, the pulsed RF power enters the input waveguide 850 of the first 3 dB waveguide hybrid junction 830. The first 3 dB waveguide hybrid junction 830 divides the RF power, generally, in half with first and second portions of the pulsed RF power propagating, respectively, through the first and second output waveguide 852, 854 of the first 3 dB waveguide hybrid junction 830 to the phase shifter 834. Operation of the phase shifter 838 according to a method described with reference to the high-speed phase shifters 200, 300, 500, 600 above, then determines how much of the RF power received from each of first and second output waveguides 852, 854 is to be, respectively, routed to the first and second input waveguides 860, 862 of the second 3 dB waveguide hybrid junction 832. Such determination is based on the phase differential of the RF power between first output waveguide 852 and first input waveguide 860, $\phi_1$, and the phase differential of the RF power between second output waveguide 854 and second input waveguide 860, $\phi_2$, on a pulse-by-pulse basis for the successive pulses of generated RF power.

For example and not limitation, if the difference in the phase differentials (i.e., $\Delta\phi=\phi_2-\phi_1$) is zero (0) degrees, then all of the RF power received by the phase shifter 838 via first and second output waveguides 852, 854 is directed to the first input waveguide 860 of the second 3 dB waveguide hybrid junction 832. If the difference in the phase differentials (i.e., $\Delta\phi=\phi_2-\phi_1$) is ninety (90) degrees, then the RF power received by the phase shifter 838 via first and second output waveguides 852, 854 is equally divided with the first input waveguide 860 of the second 3 dB waveguide hybrid junction 832 receiving one-half of the received RF power and the second input waveguide 862 of the second 3 dB waveguide hybrid junction 832 receiving one-half of the received RF power. If the difference in the phase differentials (i.e., $\Delta\phi=\phi_2-\phi_1$) is one hundred eighty (180) degrees, then all of the RF power received by the phase shifter 838 via first and second output waveguides 852, 854 is directed to the second input waveguide 862 of the second 3 dB waveguide hybrid junction 832. If the difference in the phase differentials (i.e., $\Delta\phi=\phi_2-\phi_1$) is sixty (60) degrees, then the RF power received by the phase shifter 838 via first and second output waveguides 852, 854 is divided by a ratio of 1:3 such that the second input waveguide 862 of the second 3 dB waveguide hybrid junction 832 receives an amount of RF power that is three (3) times greater than the amount of RF power received by the first input waveguide 860 of the second 3 dB waveguide hybrid junction 832. If the difference in the phase differentials (i.e., $\Delta\phi=\phi_2-\phi_1$) is one hundred twenty (120) degrees, then the RF power received by the phase shifter 838 via first and second output waveguides 852, 854 is divided by a ratio of 3:1 such that the first input waveguide 860 of the second 3 dB waveguide hybrid junction 832 receives an amount of RF power that is three (3) times greater than the amount of RF power received by the second input waveguide 862 of the second 3 dB waveguide hybrid junction 832.

In accordance with the third embodiment, the phase shifter 834 is operated such that at each even numbered pulse of the successive pulses of the RF power received by the phase shifter 834, the difference in the phase differentials is sixty (60) degrees. At each odd numbered pulse of the successive pulses of the RF power received by the phase shifter 834, the difference in the phase differentials is one hundred twenty (120) degrees. Because the energy of the charged particle beams exiting first and second accelerating sections 810, 816 is dependent on the RF power input thereto and on the injected beam current of the charged particles injected by the injectors 812, 820, the energy of the charged particle beams exiting the accelerating sections 810, 816 is greater if the RF power provided to the accelerating sections 810, 816 for a given injected beam current. Thus, at each even numbered pulse of RF power and with the injected beam current being held constant, the energy of the charged particles of the charged particle beam exiting the first accelerating section 810 is three times less than the energy of the charged particles of the charged particle beam exiting the second accelerating section 816. At each odd numbered pulse of RF power and with the injected beam current being held constant, the energy of the charged particles of the charged particle beam exiting the first accelerating section 810 is three times greater than the energy of the charged particles of the charged particle beam exiting the second accelerating section 816. As a consequence, the charged particle beams exiting the first and second accelerating sections 810, 816 include pulses of charged particles having energy levels that alternate, from pulse-to-pulse, between a higher energy level and a lower energy level. The use of such alternating energy levels and analysis of data collected from such use enables the radiographic inspection system 800 to discriminate materials present in the vehicle 802 or cargo container 804 by their material type (e.g., by their effective atomic number).

The input waveguides 860, 862 of the second 3 dB waveguide hybrid junction 832 receive RF power from the phase shifter 834 in ratios that vary, as described above, based upon whether the RF power received by the phase shifter 834 is an even or odd numbered pulse. The second 3 dB waveguide hybrid junction 832 may divide (e.g., in half) the received RF power with first and second portions of the pulsed RF power propagating, respectively, through the first and second output waveguides 864, 866 of the second 3 dB waveguide hybrid junction 832 and into respective feeder waveguides 870, 872. The RF power travels through the feeder waveguides 870, 872 and is input into the respective first and second accelerating sections 810, 816 proximate the second ends thereof.

Upon delivery to the first and second accelerating sections 810, 816, the RF power propagates throughout the accelerating sections 810, 816 and creates respective accelerating fields therein that vary and alternate in strength between pulses of RF power and injected pulse of charged particles. The pulses of charged particles emitted into the accelerating sections 810, 816 by injectors 812, 820 in synchronization with the pulses of received RF power travel through the respective accelerating sections 810, 816 and are accelerated by the accelerating fields created therein. Each accelerating section 810, 816 may have a bunching portion followed by an accelerating portion such that the pulses of charged particles are bunched before being accelerated by the accelerating fields. The accelerated pulses of charged particles exit the respective accelerating sections 810, 816 as pulsed charged particle beams with successive pulses of charged particles exiting each accelerating section 810, 816 having alternating energy levels.

Based upon the presently described third embodiment, the specifications of the components described above for an acceptable form of the third embodiment, and upon phase shifter 834 switching the phase differential difference between sixty (60) degrees for even numbered RF pulses and one hundred twenty (120) degrees for odd numbered RF pulses, the RF power provided to the first and second accelerating sections 810, 816 at the time of an even numbered RF pulse is 1.1 MW and 3.3 MW, respectively. The corresponding injected beam current for the charged particles injected into the first and second accelerating sections 810, 816 is 1 A and 0.35 A, respectively. At the time of an odd numbered RF pulse, the RF power provided to the first and second accelerating sections 810, 816 is 3.3 MW and 1.1 MW, respectively. The corresponding injected beam current for the charged particles injected into the first and second accelerating sections 810, 816 is 0.35 A and 1.0 A, respectively. As a consequence, the energy levels of the pulses of charged particles exiting the first and second accelerating sections 810, 816 at the time of an even numbered RF pulse are 3 MeV and 9 MeV, respectively. The energy levels of the pulses of charged particles exiting the first and second accelerating sections 810, 816 at the time of an odd numbered RF pulse are 9 MeV and 3 MeV, respectively.

It should be noted that although the first 3 dB waveguide hybrid junction 830 has been described as dividing the generated RF power equally between its first and second output waveguides 852, 854 and the second 3 dB waveguide hybrid junction 832 has been described as possibly dividing the RF power that it receives, the first and second 3 dB waveguide hybrid junctions 830, 832 are capable of dividing the RF power in any ratio. It should also be noted that the differences in the phase differentials of the RF power across the phase shifter 834 does not depend on the particular configuration of the phase shifter 834, as such configuration may be selected to be the same or different from the high-speed phase shifters 200, 300, 500, 600 described above. However, the amplitude of the RF waves of the RF power does depend on the phase shift performed by the phase shifter 834.

The pulsed charged particle beams, upon exiting accelerating sections 810, 816, are respectively directed through connecting waveguides 880, 890 to respective radiation field forming devices 814, 822. Upon entering the radiation field forming devices 814, 822, the pulsed charged particle beams impinge on respective radiation conversion targets 882, 892 that convert the successive pulses of the pulsed charged particle beams exiting respective accelerating sections 810, 816 into respective successive pulses of bremsstrahlung. Then, the respective successive pulses of bremsstrahlung pass through the slots of respective collimators 882, 892 with narrow, substantially planar, fan-shaped, pulsed bremsstrahlung 886, 896 being produced therefrom and output from respective radiation field forming devices 814, 822.

The substantially planar, fan-shaped, pulsed bremsstrahlung 886 emitted from radiation field forming device 814 travels in a, generally, downward direction (i.e., indicated by arrow 950) toward the top portion 914 of the elongate collimator structure's wall 908 and the first slot 926 thereof. The portion of the first slot 926 in the top portion 914 of the elongate collimator structure's wall 908 collimates the bremsstrahlung 886 so that a portion of the bremsstrahlung 886 is directed through the first slot 926 and through the vehicle 802 and cargo container 804 (and, hence, through the contents thereof). After passing through the vehicle 802 and cargo container 804, the portions of the first slot 926 in the bottom and second side portions 916, 920 of the elongate collimator structure's wall 908 collimate the bremsstrahlung 886 so that a portion of the bremsstrahlung 886 is directed through the first slot 926 for a second time. The portion of the bremsstrahlung 886 that passes through the portions of the first slot 926 in the bottom and second side portions 916, 920 of the elongate collimator structure's wall 908 impinges on the first and second portions 946A, 948A of the first detector array 942A. Detector elements in the first and second portions 946A, 948A of the first detector array 942A detect the intensity of the bremsstrahlung 886 impinging thereon and produce data in the form of electrical signals that are communicated to a signal processing portion (not shown) of the radiographic inspection system 800.

In a similar manner, the substantially planar, fan-shaped, pulsed bremsstrahlung 896 emitted from radiation field forming device 822 travels in a, generally, horizontal or lateral direction (i.e., indicated by arrow 952) toward the first side portion 918 of the elongate collimator structure's wall 908 and the second slot 928 thereof. The portion of the second slot 928 in the first side portion 918 of the elongate collimator structure's wall 908 collimates the bremsstrahlung 896 so that a portion of the bremsstrahlung 896 is directed through the second slot 928 and through the vehicle 802 and cargo container 804 (and, hence, through the contents thereof). After passing through the vehicle 802 and cargo container 804, the portions of the second slot 928 in the bottom and second side portions 916, 920 of the elongate collimator structure's wall 908 collimate the bremsstrahlung 896 so that a portion of the bremsstrahlung 896 is directed through the second slot 928 for a second time. The portion of the bremsstrahlung 896 that passes through the portions of the second slot 928 in the bottom and second side portions 916, 920 of the elongate collimator structure's wall 908 impinges on the first and second portions 946B, 948B of the second detector array 942B. Detector elements in the first and second portions 946B, 948B of the second detector array 942B detect the intensity of the bremsstrahlung 896 impinging thereon and produce data in the form of electrical signals that are communicated to the signal processing portion (not shown) of the radiographic inspection system 800.

The signal processing portion of the radiographic inspection system 800 receives the data (e.g., electrical signals) from the first and second detector arrays 942A, 942B and generates therefrom images of the contents of the vehicle 802 and cargo container 804. Because the data produced by the first detector array 942A corresponds to the bremsstrahlung 886 emitted from the first accelerating section 810 in a, generally, downward direction (i.e., indicated by arrow 950), a first image of the contents of the vehicle 802 and cargo container 804 is generated that comprises a first view looking at a slice of the vehicle 802 and cargo container 804 downward and side-to-side. Since the data produced by the second detector array 942B corresponds to the bremsstrahlung 896 emitted from the second accelerating section 816 in a, generally, horizontal or lateral direction (i.e., indicated by arrow 952), a second image of the contents of the vehicle 802 and cargo container 804 is generated that comprises a second view looking at a slice of the vehicle 802 and cargo container 804 from the side and top-to-bottom. Thus, the radiographic inspection system 800 of the third embodiment produces views of the contents of the vehicle 802 and cargo container 804 from multiple directions and in multiple planes.

By moving the vehicle 802 and cargo container 804 at an appropriate speed along the longitudinal axis 906 of the elongate collimator structure 900 in the direction indicated by arrow 912 and by aggregating and ordering the first views of the contents of the vehicle 802 and cargo container 804 generated by data collected by the detector arrays 942A, 942B at successive slices through the vehicle 802 and cargo container 804, the radiographic inspection system 800 generates an image, or view, of the contents of the vehicle 802 and cargo container 804 in a first plane looking downward at the tops of the vehicle 802 and cargo container 804 and extending the entire length of the vehicle 802 and cargo container 804. Similarly, by aggregating and ordering the second views of the contents of the vehicle 802 and cargo container 804 generated by data collected by the detector arrays 942A, 942B at successive slices through the vehicle 802 and cargo container 804 taken while moving the vehicle 802 and cargo container 804, the radiographic inspection system 800 generates an image, or view, of the contents of the vehicle 802 and cargo container 804 in a second plane looking at the sides of the vehicle 802 and cargo container 804 and extending the entire length of the vehicle 802 and cargo container 804.

Contemporaneously with generating images of the contents of the vehicle 802 and cargo container 804, the signal processing portion of the radiographic inspection system 800 determines material types (e.g., effective atomic numbers) for the materials of the contents that are present in the vehicle 802 and cargo container 804. Such capability is made possible by the RF drive subsystem's ability to deliver an amount of RF power to the accelerating sections 810, 816 that alternately varies, by virtue of the operation of phase shifter 834, between successive pulses of thereof and the consequential alternation in the energy levels of the pulses of charged particles present in the pulsed charged particle beams exiting the accelerating sections 810, 816.

Importantly, the radiographic inspection system 800 generates multiple views of the contents of a vehicle 802 and cargo container 804 and discriminates the types of materials present therein using an RF drive subsystem 808 that utilizes only a single power supply 824 and a single RF source 826 to provide RF power for two independent accelerating sections 810, 816. Through the inventive use of only one power supply 824 and one RF source 826 (and, hence, one control system therefor), the radiographic inspection system 800 of the third embodiment eliminates the need for two power supplies and two RF sources that would, ordinarily, be required to provide RF power for two independent accelerating sections. As a consequence, the radiographic inspection system 800 of the third embodiment of the present invention is substantially less costly to build, operate, and maintain than other radiographic inspection systems having multiple accelerating sections. Thus, the radiographic inspection system 800 makes possible the generation of multiple views of the contents of a vehicle 802 and cargo container 804 in multiple planes and the discrimination of the materials of the contents thereof while substantially reducing the cost of doing so. It should be understood, however, that while the radiographic inspection system 800 has been described herein as producing images and discriminating the materials of the contents of a vehicle 802 and cargo container 804, the radiographic inspection system 800 may be employed to generate images and discriminate the materials of the contents of other containers, boxes, packages, luggage, or many other subject objects.

Whereas the present invention has been described in detail above with respect to exemplary embodiments thereof, it is understood that variations and modifications can be effected within the spirit and scope of the invention, as described herein before and as defined in the appended claims. The corresponding structures, materials, acts, and equivalents of all means-plus-function elements, if any, in the claims below are intended to include any structure, material, or acts for performing the functions in combination with other claimed elements as specifically claimed.

What is claimed is:

1. A radiographic inspection system for inspecting the contents of a container, said radiographic inspection system comprising:
   a power source for generating electromagnetic waves;
   a first injector for producing pulses of charged particles;
   a first accelerating section operable to receive said pulses of charged particles from said first injector, said first accelerating section being further operable to receive a first portion said electromagnetic waves and to transfer energy thereof to said pulses of charged particles from said first injector;
   a second injector for producing pulses of charged particles;
   a second accelerating section operable to receive said pulses of charged particles from said second injector, said second accelerating section being further operable to receive a second portion of said electromagnetic waves and to transfer energy thereof to said pulses of charged particles from said second injector; and,
   a phase shifter interposed between said power source and said first and second accelerating sections for receiving said electromagnetic waves from said power source, for alternately changing the phase of said electromagnetic waves between successive pulses of said pulses of charged particles from said first injector, and for delivering said electromagnetic waves to said first accelerating section.

2. The radiographic inspection system of claim 1, wherein said radiographic inspection system further comprises a 3 dB waveguide hybrid junction connected between said power source and said phase shifter.

3. The radiographic inspection system of claim 1, wherein said radiographic inspection system further comprises a 3 dB waveguide hybrid junction connected between said phase shifter and said first accelerating section.

4. The radiographic inspection system of claim 3, wherein said 3 dB waveguide hybrid junction is connected between said phase shifter and said second accelerating section.

5. The radiographic inspection system of claim 1, wherein said radiographic inspection system further comprises a conversion target, and wherein said first accelerating section is further operable to emit accelerated charged particles at said conversion target to produce bremsstrahlung directed at a container.

6. The radiographic inspection system of claim 5, wherein said conversion target is a first conversion target and said radiographic inspection system further comprises a second conversion target, wherein said bremsstrahlung is directed at said container in a first direction, and wherein said second accelerating section is further operable to emit accelerated charged particles at said second conversion target to produce bremsstrahlung directed at said container in a second direction different than said first direction.

7. The radiographic inspection system of claim 6, wherein said first direction is substantially perpendicular to said second direction.

8. The radiographic inspection system of claim 5, wherein said conversion target is a first conversion target and said radiographic inspection system further comprises a second conversion target, wherein said bremsstrahlung is directed at said container substantially in a first plane, and wherein said second accelerating section is further operable to emit accelerated charged particles at said second conversion target to produce bremsstrahlung directed at said container substantially in a second plane different than said first direction.

9. The radiographic inspection system of claim 8, wherein said first plane is substantially perpendicular to said second plane.

10. The radiographic inspection system of claim 1, wherein said phase shifter comprises a high-speed phase shifter having a rotary reflector therein.

11. The radiographic inspection system of claim 1, wherein said phase shifter comprises a high-speed phase shifter having a waveguide shorting device and a waveguide discharger, wherein said waveguide shorting device is connected at an end of said waveguide discharger.

12. The radiographic inspection system of claim 1, wherein said phase shifter comprises a high-speed phase shifter having a waveguide segment, wherein said waveguide segment has an outer wall, a ferrite element positioned within said waveguide segment, an electromagnet secured to the outer wall of said waveguide segment, and a coil for creating a magnetic field in said ferrite element.

* * * * *